(12) United States Patent
Kuriyama

(10) Patent No.: US 10,799,085 B2
(45) Date of Patent: Oct. 13, 2020

(54) ENDOSCOPE APPARATUS AND FOCUS CONTROL METHOD

(71) Applicant: OLYMPUS CORPORATION, Tokyo (JP)

(72) Inventor: Naoya Kuriyama, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 422 days.

(21) Appl. No.: 15/831,969

(22) Filed: Dec. 5, 2017

(65) Prior Publication Data

US 2018/0103829 A1 Apr. 19, 2018

Related U.S. Application Data

(63) Continuation of application No. PCT/JP2015/066837, filed on Jul. 11, 2015.

(51) Int. Cl.
| | | |
|---|---|---|
| A61B 1/00 | (2006.01) | |
| A61B 1/04 | (2006.01) | |
| G02B 23/24 | (2006.01) | |
| G02B 7/28 | (2006.01) | |
| A61B 1/045 | (2006.01) | |

(52) U.S. Cl.
CPC ...... *A61B 1/00006* (2013.01); *A61B 1/00009* (2013.01); *A61B 1/00055* (2013.01); *A61B 1/00188* (2013.01); *A61B 1/042* (2013.01); *A61B 1/045* (2013.01); *G02B 7/28* (2013.01); *G02B 23/243* (2013.01); *G02B 23/2484* (2013.01)

(58) Field of Classification Search
CPC .................................................. A61B 1/00188
USPC ............................................................ 348/65
See application file for complete search history.

(56) References Cited

U.S. PATENT DOCUMENTS

2004/0130651 A1* 7/2004 Wakashiro ......... A61B 1/00188
348/349
2016/0234427 A1* 8/2016 Yoshino ............. G02B 23/2484

FOREIGN PATENT DOCUMENTS

| JP | 2004-205981 A | 7/2004 |
|---|---|---|
| JP | 2006-211458 A | 8/2006 |
| JP | 2010-191080 A | 9/2010 |
| JP | 2010-243922 A | 10/2010 |
| JP | 2013-043007 A | 3/2013 |
| JP | 2013-130827 A | 7/2013 |

OTHER PUBLICATIONS

International Search Report dated Sep. 15, 2015 issued in PCT/JP2015/066837.

* cited by examiner

*Primary Examiner* — Jeffery A Williams
(74) *Attorney, Agent, or Firm* — Scully, Scott, Murphy & Presser, P.C.

(57) ABSTRACT

An endoscope apparatus includes a processor comprising hardware. The processor implements a motion information acquisition process that acquires motion information representing a relative motion with respect to an imaging section and an object, a motion information determination process that determines motion information reliability indicating reliability of the motion information, and a focus control process that determines whether or not to perform a focus operation to cause the imaging section to bring the object into focus based on the motion information and the motion information reliability.

10 Claims, 20 Drawing Sheets

ENDOSCOPE APPARATUS AND FOCUS CONTROL METHOD

CROSS REFERENCE TO RELATED APPLICATION

This application is a continuation of International Patent Application No. PCT/JP2015/066837, having an international filing date of Jun. 11, 2015, which designated the United States, the entirety of which is incorporated herein by reference.

BACKGROUND

A depth of field as deep as possible is required for an endoscope apparatus (endoscope system) so that the user can easily perform diagnosis and treatment. In recent years, the depth of field of an endoscope apparatus has become shallow along with the use of an image sensor having a large number of pixels, and an endoscope apparatus that performs an autofocus (AF) process has been proposed.

Examples of a known AF control process include the following methods. A first method is used to implement an AF process that is used for a video camera or the like, and performs a focus operation using a change in contrast within an image as a trigger. A second method is disclosed in JP-A-2010-191080. The second method detects a relative change in position with respect to the object and a camera using a motion sensor, and performs a focus operation when the output (e.g., angular acceleration or acceleration) from the motion sensor has become equal to or larger than a predetermined amount.

SUMMARY

According to one aspect of the invention, there is provided an endoscope apparatus comprising a processor comprising hardware, the processor being configured to implement:

a motion information acquisition process that acquires motion information representing a motion with respect to an imaging section and an object, a motion information determination process that determines motion information reliability indicating reliability of the motion information, and a focus control process that determines whether or not to perform a focus operation to cause the imaging section to bring the object into focus based on the motion information and the motion information reliability.

According to another aspect of the invention, there is provided a focus control method comprising: performing a process that acquires motion information representing a motion with respect to an imaging section and an object, performing a process that determines motion information reliability indicating reliability of the motion information, and performing a process that determines whether or not to perform a focus operation to cause the imaging section to bring the object into focus based on the motion information and the motion information reliability.

DESCRIPTION OF EXEMPLARY EMBODIMENTS

Figure 1:
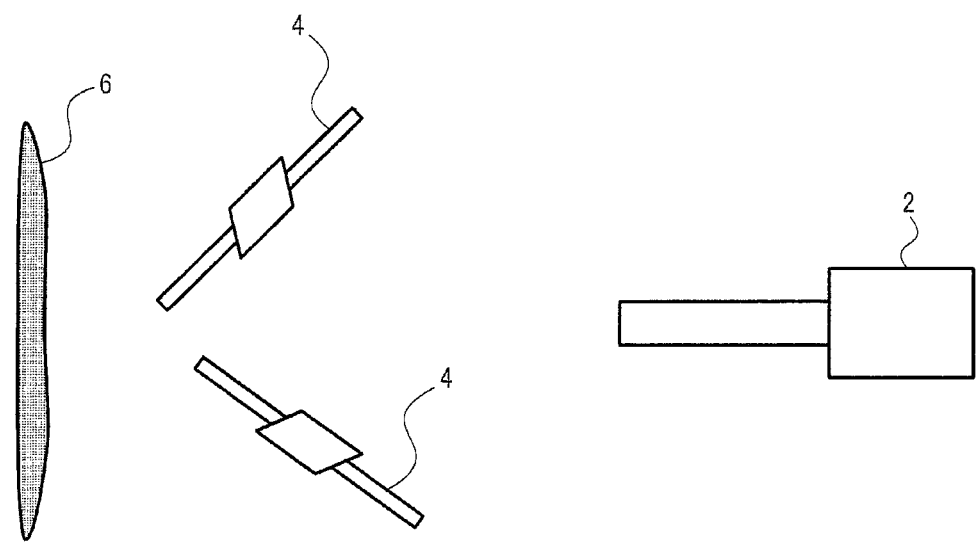
FIG. 1 is a view illustrating an endoscopic procedure.

When the known AF control method described above is applied to an endoscope apparatus, it may be difficult to implement an appropriate focus control process that is required during various scenes that may occur when an endoscopic procedure is performed. For example, when the first method is applied to an endoscopic procedure, an unnecessary focus operation may be performed since a change in contrast occurs due to the manipulation of a treatment tool. When the second method is applied to an endoscopic procedure, an unnecessary focus operation may be performed when a large temporary motion (e.g., shake) has occurred.

With various aspects of first to third embodiments, an endoscope apparatus and a focus control method can be provided with which a necessary focus control process can be performed, during various scenes that may occur when an endoscopic procedure is performed.

According to one aspect of the embodiment, there is provided an endoscope apparatus comprising a processor comprising hardware, the processor being configured to implement:

a motion information acquisition process that acquires motion information representing a motion with respect to an imaging section and an object, a motion information determination process that determines motion information reliability indicating reliability of the motion information, and a focus control process that determines whether or not to perform a focus operation to cause the imaging section to bring the object into focus based on the motion information and the motion information reliability.

According to one aspect of the embodiment, whether or not to cause the imaging section to perform the focus operation to bring the object into focus is determined, based on the motion information about a relative motion with respect to the imaging section and the object, and reliability of the motion information. With whether or not the focus operation is required determined based on the motion information and the reliability of the motion information as described above, a necessary focus control process can be performed, during various scenes that may occur when an endoscopic procedure is performed with a risk of performing an unnecessary focus operation reduced.

The exemplary embodiments of the invention are described below. Note that the exemplary embodiments described below do not in any way limit the scope of the invention laid out in the claims. Note also that not all of the elements described below in connection with the exemplary embodiments should be taken as essential elements of the invention.

For example, an example where a configuration and a focus control method according to the present invention are applied to an endoscope apparatus and an operation method is described below. However, this should not be construed in a limiting sense, and the configuration and the focus control method according to the present invention may be applied to an imaging apparatus (such as a video camera, microscope, or camera for vision of a robot, for example) and to a configuration of a focus control apparatus and an operation method for the imaging apparatus.

1. First Embodiment

For example, the first method that uses a change in contrast as a trigger, and the second method that uses a situation in which the output from the motion sensor has become equal to or larger than a predetermined amount, as a trigger (see above), are known as the AF control method. A case where the known method is applied to an endoscopic procedure is discussed below.

As illustrated in FIG. 1, when an endoscopic procedure is performed using an endoscope apparatus 2, a treatment (e.g., excision of a lesion, or suture) is performed on an object 6 (tissue) using a treatment tool 4 (e.g., electrosurgical knife or forceps). When the first method is applied to the endoscopic procedure, since the treatment tool 4 is included in the captured image in addition to the object 6, and makes a motion based on the operation performed by the user, a change in contrast occurs even when the imaging range or the focus state has not changed. An unnecessary focus operation may be performed due to a change in contrast caused by the treatment tool 4, and it is difficult to implement a stable AF control process when the treatment tool 4 is operated.

In a case where the second method is applied, when a motion whereby the output from the motion sensor momentarily becomes equal to or larger than a predetermined amount has occurred due to shake or the like, the focus operation is performed although the imaging range has not technically changed (or the object lies within the depth of field). The usability of the endoscope apparatus may be impaired if the focus operation unintended by a user is performed. Since the focus operation is not performed when the output from the motion sensor is less than a predetermined amount, the focus operation may not be performed even when the object is out of focus. For example, when a motion whereby the output from the motion sensor is less than a predetermined amount has continuously occurred in an identical direction, the focus operation is not performed although the imaging range has moved to a large extent (or the object lies outside the depth of field).

As described above, the known AF control methods have a problem in that an unnecessary focus operation is performed, or a necessary focus operation is not performed, during various scenes that may occur when an endoscopic procedure is performed.

Figure 2:
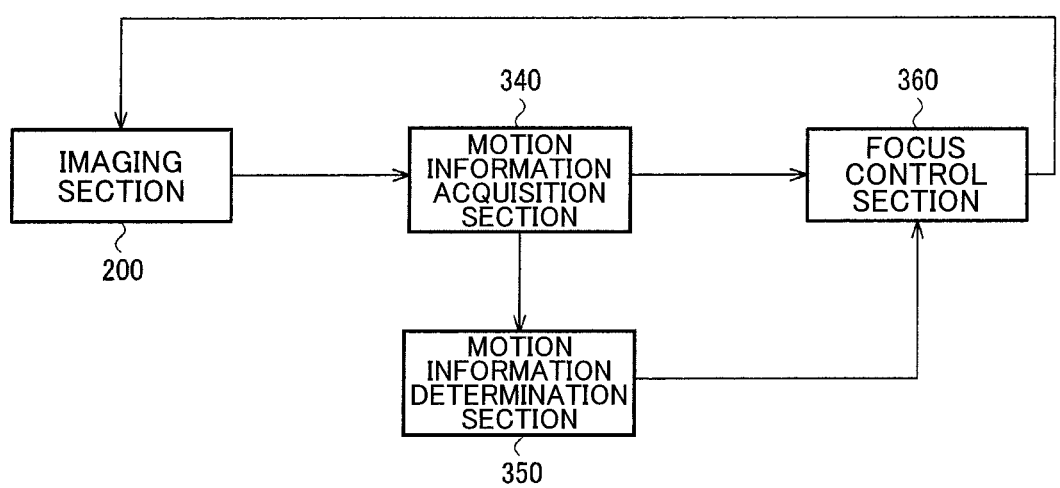
FIG. 2 illustrates a configuration example of an endoscope apparatus (first embodiment).

FIG. 2 illustrates a configuration example of an endoscope apparatus according to a first embodiment that can solve the above problem. The endoscope apparatus includes: an imaging section 200; a motion information acquisition section 340 that acquires motion information representing a motion with respect to the imaging section 200 and an object; a motion information determination section 350 that determines motion information reliability indicating reliability of the motion information; and a focus control section 360 that determines whether or not to cause the imaging section 200 to perform a focus operation (AF operation) to bring an object into focus based on the motion information and the motion information reliability.

A necessary focus control process that is required during various scenes that may occur when an endoscopic procedure is performed can be implemented by determining whether or not to perform the focus operation based on the motion information and the motion information reliability as described above.

The object an image of which is captured using an endoscope apparatus may be tissue and a treatment tool, for example. The focus operation is required when the imaging range with respect to the tissue has changed (moved), or when the tissue or the treatment tool lies outside the depth of field, for example. If the focus operation is performed when such a situation has not occurred, a decrease in visibility may occur due to a temporary change in focus state. For example, the treatment tool is operated during a procedure without changing (moving) the imaging range. In this case, the procedure is hindered if a change in focus state has occurred during the procedure. According to the first embodiment utilizing the reliability of the motion information, the focus operation is not performed when the focus operation is not required (e.g., when only the treatment tool makes a motion or when the motion information is erroneously detected due to noise).

For example, in a second embodiment described later, the reliability of the motion information is determined based on at least one of image brightness, reliability of local motion vector matching, and variation of local motion vectors in an image.

The motion vector may be detected through block matching on an image. In such a configuration, criteria for determining the reliability of the motion information thus detected include: the quality of the image itself; whether or not areas matched in the block matching correspond to the same object (matching degree); and the types of a motion represented by the motion vector detected. The detection based on the brightness of an image corresponds to a process of determining a low-quality image in which a motion vector cannot be correctly detected due to overexposure, underexposure, or the like for example. The reliability of the block matching is determined by determining the matching degree between areas determined to correspond to the same portion in the block matching based on similarity between the areas, for example. Low similarity indicates low reliability of the block matching. The variation of local motion vectors indicates that the treatment tool is making a motion different from that of the tissue (background) for example. Thus, such a random motion different from a uniform motion of the tissue (background) is determined as a low-reliability motion. With the reliability thus determined, a scene requiring the focus operation can be determined, without being affected by image quality, noise, a condition where no motion vector can be detected (for example, a fast motion toward the outside the matching area), or a motion vector, different from the uniform motion of the tissue, due to the treatment tool, noise, or the like. Thus, the focus operation can be performed in a required situation where the imaging range with respect to the tissue has changed, or when the tissue or the treatment tool lies outside the depth of field.

The term "motion information" used herein refers to information that changes corresponding to a relative change in position (e.g., a movement that does not change the optical axis direction of the camera) or a relative change in direction (e.g., a rotation (pan or tilt) that changes the optical axis direction of the camera) with respect to the imaging section 200 and the object. For example, when a motion vector is detected from an image, the magnitude or the direction of the motion vector changes corresponding to the movement or the rotation of the imaging section 200. When a motion sensor is used, an acceleration, an angular acceleration, an angular velocity, and the like that correspond to the movement or the rotation of the imaging section 200 are obtained. The motion information is an amount that represents the information about the magnitude of the motion and the information about the direction of the motion, or may be information about one of the magnitude of the motion and the direction of the motion. The motion information according to the present embodiment preferably includes the information about the magnitude of the motion and the information about the direction of the motion. With the motion information including the information about the magnitude of the motion and the information about the direction of the motion, a motion amount in a single direction can be accumulated as described later, so that relative movement with respect to the imaging section 200 and an object (movement of the imaging range, or movement by which the object lies outside the depth of field) can be detected.

The focus control section 360 according to the present embodiment obtains global motion information about a global relative motion with respect to the imaging section 200 and an object based on the motion information and the motion information reliability, determines global motion information reliability indicating the reliability of the global motion information based on the motion information reliability, and determines whether or not to perform the focus operation based on at least one of the global motion information or the global motion information reliability.

The global motion information is information about a motion in a range wider than a local motion of a tissue (e.g., pulsation of blood vessels, digestive tract, or the like) or a motion of a treatment tool. Specifically, the global motion information is information about a relative motion with respect to the imaging section and the tissue in the image as a whole. For example, when a local motion vector is obtained by performing the block matching on an image, the global motion is a motion in a rage wider than the size of a block used in the block matching. For example, a mean value of local motion vectors with high reliability in an image is obtained as the global motion information.

When whether or not the focus operation is to be performed is determined based on the global motion information about a global relative motion with respect to the imaging section 200 and the object, the focus operation can be performed in response to a global motion of the tissue with influence of a local motion reduced.

With the reliability of the global motion information obtained, whether or not to perform the focus operation can be determined based on the global motion information with high reliability. For example, the reliability of the global motion information is determined based on the number of local motion vectors with high reliability, in the local motion vectors in an image. For example, an image with a small number of local motion vectors with high reliability can be regarded as an image including a large amount of noise and local motions. Thus, the global motion information about such an image cannot be regarded as accurate information about a global motion. With such global motion information that is likely to have low reliability excluded, whether or not the focus operation is required can be determined based on the global motion of the tissue.

The focus control section 360 according to the first embodiment obtains cumulative global motion information, as a result of a process of accumulating the global motion information over a plurality of frames, and determines whether or not to perform the focus operation based on at least one of the cumulative global motion information or the global motion information reliability.

With the cumulative global motion information thus used, a necessary focus control process can be performed during various scenes that may occur when an endoscopic procedure is performed. Specifically, cumulative global motion information with a large amount is obtained when a large movement of the imaging range of the tissue, or movement by which the tissue or the treatment tool lies outside the depth of field occurs, and thus it can be determined that the focus operation is required based on such information.

For example, a change in scene as a result of small motions continuously occurring in an identical direction is difficult to detect based on determination using a threshold value directly set for a motion amount. In view of this, the present embodiment accumulates the motion amount so that the motions can be detected as a large motion amount of (so that the movement of the imaging range or an out of focus state can be detected) to perform the focus operation. Furthermore, the focus operation unintended by a user can be prevented even when a momentary large motion occurs, as long as other motions accumulated are small and thus results in a small cumulative motion amount (which results in a determination that the movement of the imaging range has not occurred or the out of focus state has not occurred). With the motion amount accumulated, random motions are expected to be averaged. For example, a treatment tool is expected to be likely to move randomly rather than continuously in a single direction. Thus, a small cumulative motion amount is obtained with the motion of the treatment tool, and a large cumulative motion amount is obtained with the motion of the imaging range with respect to the tissue in a single direction (the relative motion with respect to the imaging section and the tissue in a single direction).

The plurality of frames correspond to the number of frames over which the global motion information is accumulated. This number of accumulating frames is not limited to a fixed number and may be a variable number. For example, the global motion information corresponding to a certain reference frame and after may be accumulated. In this case, the number of accumulating frames is 3 in the third frame from the reference frame, and is 10 in the tenth frame from the reference frame. Alternatively, the number of accumulating frames may be set to a predetermined number, and the global motion information may be accumulated from the predetermined previous frame up to the current frame. In this case, the number of accumulating frames is set to the predetermined number even when the current frame has changed.

The term "accumulating process" includes a process of sequentially summing (integrating) up the global motion information obtained in time series. The process is not limited to simple summing. Various types of calculation such as weighted addition based on a certain coefficient may be performed or global motion information corrected in a certain manner may be summed up.

The term "focus control process" includes a focus operation that adjusts the focus state, a standby state in which the focus state is not adjusted, a transition control process, and the like, and refers to the entire process that controls the focus state of the imaging section. The term "focus operation" refers to a series of operations that bring the object into focus. For example, the focus operation may be implemented using a contrast method (hill-climbing method), a method that determines the in-focus direction by means of wobbling, or the like.

The endoscope apparatus according to the present embodiment may have the configuration described below. Specifically, the endoscope apparatus according to the present embodiment includes a memory that stores information (for example, a program and various types of data); and a processor (a processor including hardware) that operates based on the information stored in the memory. The processor implements a motion information acquisition process that acquires motion information representing a relative motion with respect to an imaging section and an object, a motion information determination process that determines motion information reliability indicating reliability of the motion information, and a focus control process that determines whether or not to perform a focus operation to cause the imaging section to bring the object into focus based on the motion information and the motion information reliability.

For example, the processor may have functions of sections each implemented by individual hardware, or the functions of sections implemented by integrated hardware. For example, the processor includes hardware that may include at least one of a circuit that processes a digital signal and a circuit that processes an analog signal. For example, the processor may include one or a plurality of circuit devices (for example, an IC or the like) and one or a plurality of circuit elements (for example, a resistor, a capacitor, or the like) mounted on a circuit board. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an application specific integrated circuit (ASIC). The processor may include an amplifier circuit, a filter circuit, or the like that processes an analog signal. The memory may be a semiconductor memory (e.g., a static random access memory (SRAM) or a dynamic RAM (DRAM)), or may be a register. The memory may be a magnetic storage device such as a hard disk drive (HDD), or may be an optical storage device such as an optical disc device. For example, the memory may store a computer-readable instruction. A function of each section of the endoscope apparatus is implemented as a process when the processor executes the instruction. The instruction may be an instruction set that is included in a program, or may be an instruction that instructs the hardware circuit included in the processor to operate. The sections of the endoscope apparatus include section of a processing section (a processing section 300 in FIG. 3 and FIG. 21) in the endoscope apparatus. For example, the sections include a motion information acquisition section 340, a motion information determination section 350, a focus control section 360, a preprocessing section 320, an image processing section 330, a motion information acquisition section 340, a motion information determination section 350, a focus control section 360, and a control section 370.

For example, operations according to the present embodiment are implemented as follows. The processor acquires motion information about a relative motion with respect to the imaging section and an object, and stores the information in the memory. The processor determines the motion information reliability indicating reliability of the motion information, and stores the result in the memory. The processor reads out the motion information and the motion information reliability (determination result) from the memory, determines whether or not to perform the focusing operation to cause the imaging section to bring the object into focus based on the motion information and the motion information reliability, and stores the result of the determination in the memory. The processor reads out the result of determining whether or not to perform the focus operation from the memory and controls the focus operation by the imaging section based on the determination result.

The sections of the endoscope apparatus according to the present embodiment may be implemented as a module of a program that operates on the processor. For example, the motion information acquisition section 340 is implemented as a motion information acquisition module that acquires the motion information. Similarly, the motion information determination section 350 is implemented as a motion information determination module that determines the motion information reliability. The focus control section 360 is implemented as a focus control module that determines whether or not to perform a focus operation to cause the imaging section to bring an object into focus based on the motion information and the motion information reliability.

2. Second Embodiment

2.1. Endoscope Apparatus

Figure 3:
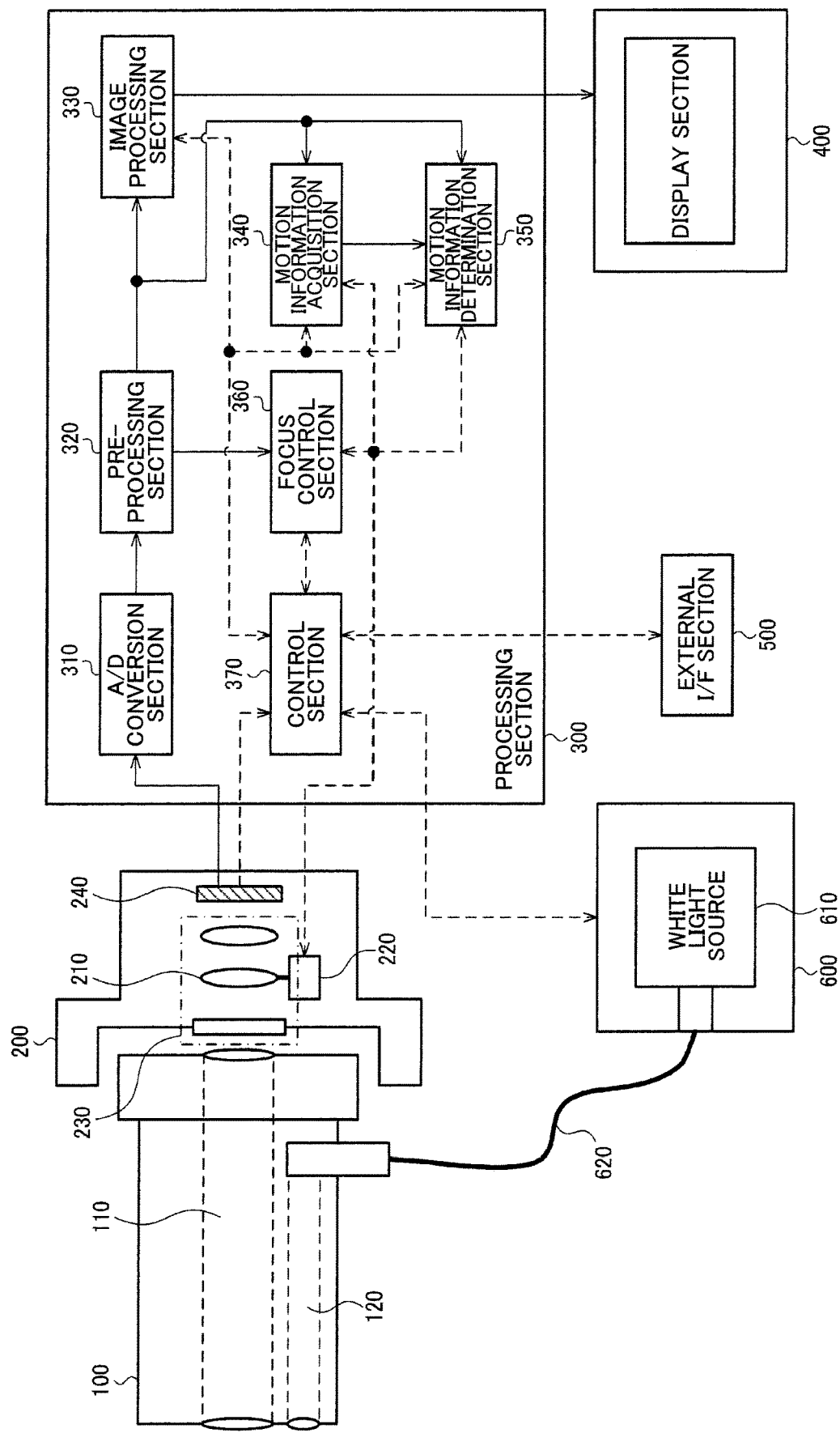
FIG. 3 illustrates a configuration example of an endoscope apparatus (second embodiment).

FIG. 3 illustrates a configuration example of an endoscope apparatus (endoscope system) according to a second embodiment. The endoscope apparatus includes a rigid scope 100 that is inserted into a body, an imaging section 200 (imaging device) that is connected to the rigid scope 100, a processing section 300 (processor), a display section 400 (display device), an external I/F section 500 (interface), and a light source section 600 (light source, light source device).

The endoscope apparatus that utilizes the rigid scope 100 is used for surgery such as laparoscopic surgery for example. More specifically, a small hole is formed in the abdominal region of a living body, for example. The rigid scope 100 is inserted into the small hole, and a treatment tool is inserted into the same small hole or another small hole. A surgical procedure is performed using the treatment tool within the field of view of the rigid scope 100. Examples of the treatment tool include a surgical knife, forceps, a needle/suture, a washing water supply/suction tool, and the like. Note that the focus control method according to the second embodiment can also be applied to an endoscope apparatus that utilizes a flexible scope instead of an endoscope apparatus that utilizes the rigid scope 100.

The light source section 600 includes a white light source 610 that emits white light, and a light guide cable 620 that guides the light emitted from the white light source 610 to the rigid scope 100. The rigid scope 100 includes a lens system 110 that includes an imaging lens, a relay lens, an eyepiece, and the like, and a light guide section 120 that guides the light emitted from the light guide cable 620 to the end of the rigid scope 100. The imaging section 200 includes an objective lens system 230 that forms an image from the light that has passed through the lens system 110 (i.e., the reflected light from the object). The objective lens system 230 includes a focus lens 210 that adjusts the in-focus object plane position. The imaging section 200 also includes an image sensor 240 that photoelectrically converts the reflected light that has passed through the objective lens system 230 to generate an image, and a focus lens driver section 220 that drives the focus lens 210. The focus lens driver section 220 is implemented by a voice coil motor (VCM), for example.

Note that the term "in-focus object plane position" used herein refers to the position of the object at which the imaging section 200 brings the object into focus. More specifically, the in-focus object plane (or the object-side focal point) is determined with respect to the objective lens system 230 corresponding to the image plane (or the image-side focal point). The term "in-focus object plane position" used herein refers to the in-focus object plane when the image plane coincides with the image plane of the image sensor 240. The in-focus object plane position is a relative position with respect to the imaging section 200 and the in-focus object plane. For example, the in-focus object plane position is represented by the distance from a reference point (e.g., the end of the objective lens system 230, or the end of the rigid scope 100) of the imaging section 200 to the in-focus object plane (i.e., the in-focus object-side plane with respect to the optical system). The in-focus object plane position can be determined from the control information (position) about the focus lens 210, and the optical properties (design values) of the objective lens system 230, for example.

The image sensor 240 has a structure in which a plurality of pixels are arranged in a two-dimensional array, and R, G, and B color filters are disposed in a Bayer array on a pixel basis. The image sensor 240 may be any image sensor other than an image sensor having a Bayer color filter array, such as an image sensor that utilizes a complementary color filter, a stacked image sensor that is designed so that each pixel can receive light having a different wavelength without using a color filter, and a monochrome image sensor that does not utilize a color filter, as long as the object can be captured to obtain an image.

The processing section 300 includes an A/D conversion section 310, the pre-processing section 320, the image processing section 330, the motion information acquisition section 340, the motion information determination section 350, the focus control section 360 (AF control section), and the control section 370. The A/D conversion section 310 converts analog signals sequentially output from the image sensor 240 into a digital image, and sequentially outputs the digital image to the pre-processing section 320. The pre-processing section 320 performs image processing (e.g., white balance process and interpolation process (demosaicing process (i.e., a process that generates an RGB image from a Bayer image)) on the image output from the A/D conversion section 310, and sequentially outputs the resulting image to the image processing section 330, the motion information acquisition section 340, the motion information determination section 350, and the focus control section 360. The image processing section 330 performs image processing (e.g., color conversion process, grayscale transformation process, edge enhancement process, scaling process, and noise reduction process) on the image output from the pre-processing section 320, and sequentially outputs the resulting image to the display section 400. The motion information acquisition section 340 acquires the inter-frame motion information based on the image output from the pre-processing section 320, and outputs the motion information to the motion information determination section 350 and the focus control section 360. The details of the motion information acquisition section 340 are described later. The motion information determination section 350 determines the reliability of the motion information (hereinafter, referred to as motion information reliability) based on the motion information output from the motion information acquisition section 340, and outputs the determination result to the focus control section 360. The details of the motion information determination section 350 are described later. The focus control section 360 performs a control process that starts or stops the focus operation based on the motion information output from the motion information acquisition section 340 and the motion information reliability output from the motion information determination section 350, and drives the focus lens driver section 220 during the focus operation so as to bring the object into focus. The details of the focus control section 360 are described later. The display section 400 is a liquid crystal monitor for example, and displays the image sequentially output from the image processing section 330.

The control section 370 is bidirectionally connected to the external I/F section 500, the image processing section 330, the focus control section 360, the image sensor 240, and the like, and exchanges a control signal with the external I/F section 500, the image processing section 330, the focus control section 360, the image sensor 240, and the like. The external I/F section 500 is an interface that allows the user to perform an input operation on the endoscope apparatus, for example. For example, the external I/F section 500 includes a setting button for setting the position and the size of the AF area, an adjustment button for adjusting the image processing parameters, and the like.

2.2. Motion Information Acquisition Section

The details of the motion information acquisition section 340 are described below. The motion information acquisition section 340 calculates a local motion on the object, based on the image output from the pre-processing section 320, to be a motion vector. Although an example in which the motion information acquisition section 340 processes only G signals of the image output from the pre-processing section 320 is described below for the sake of description, various modifications may be appropriately made, such as a modification in which the motion information acquisition section 340 processes a luminance signal calculated from the RGB signals.

Figure 4:
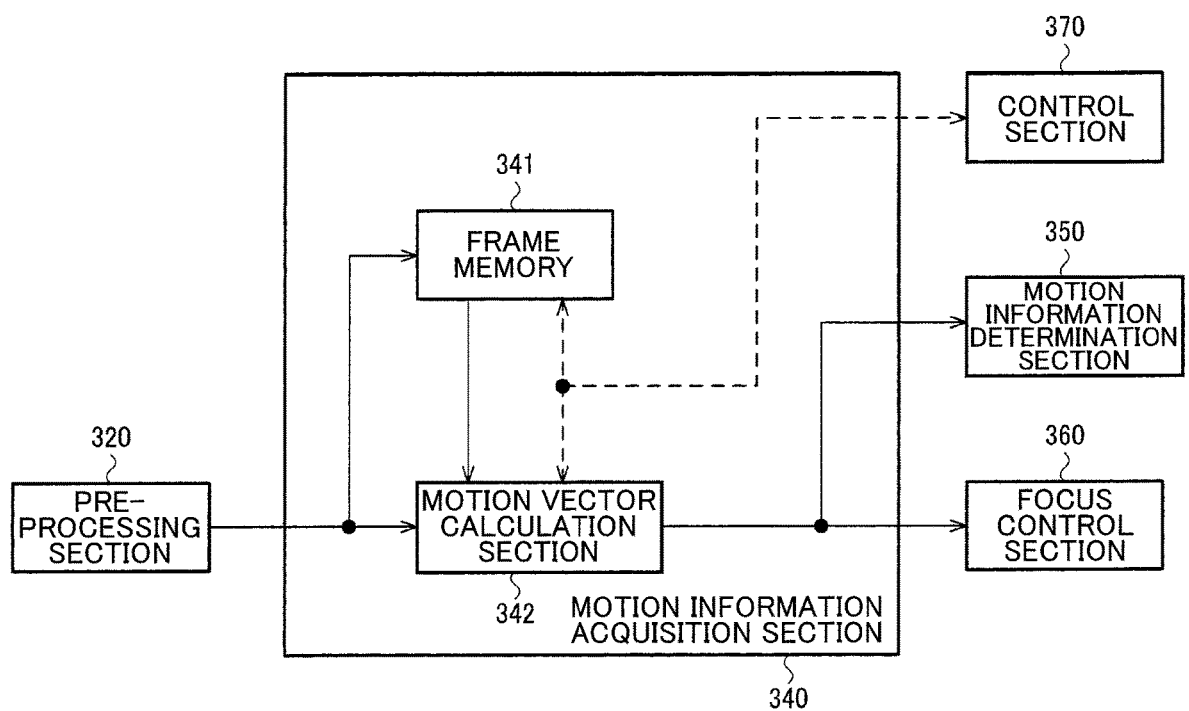
FIG. 4 illustrates a detailed configuration example of a motion information acquisition section.

FIG. 4 illustrates a detailed configuration example of the motion information acquisition section 340. The motion information acquisition section 340 includes a frame memory 341 and a motion vector calculation section 342.

The frame memory 341 is a memory that temporarily stores the image output from the pre-processing section 320. The frame memory 341 subjects the image output from the pre-processing section 320 to a frame delay, and outputs the resulting image to the motion vector calculation section 342.

Figure 5:
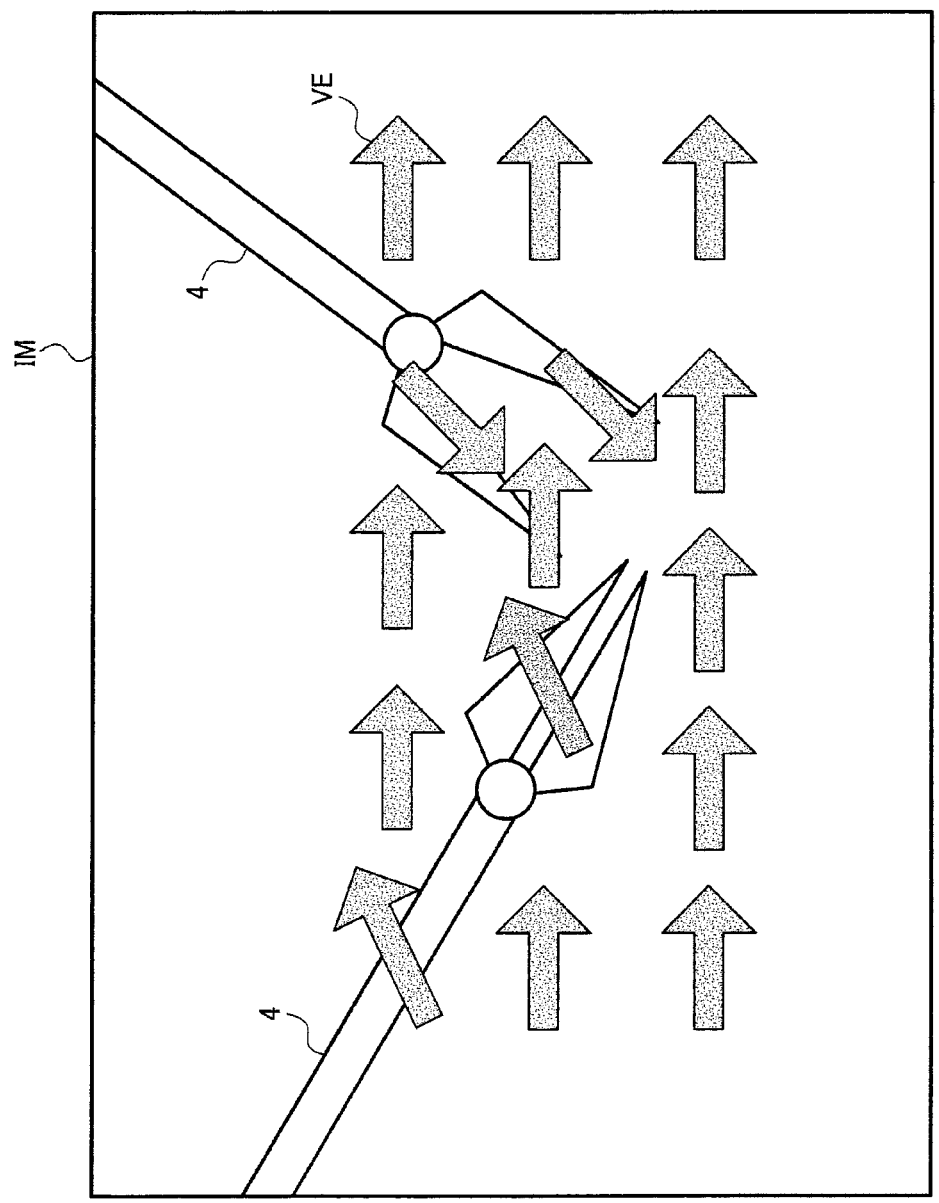
FIG. 5 illustrates an example of a local motion vector.

The motion vector calculation section 342 calculates the motion vector with respect to the image (i.e., the image that corresponds to the current frame) output from the pre-processing section 320, and the image (i.e., the image that corresponds to the previous frame) output from the frame memory 341 that has been subjected to a frame delay. The motion vector is calculated based on the image that corresponds to the current frame. More specifically, a local motion vector VE is calculated at a plurality of points within an image IM as illustrated in FIG. 5. The motion vector is calculated using a block matching method or a gradient method known in the art, for example. Although FIG. 5 illustrates an example in which the motion vector VE is calculated at a plurality of points that are set at equal intervals within the image IM, the motion vector may be calculated in another way. Various modifications may be appropriately made, such as a modification in which the motion vector is calculated at each pixel of the image, for example.

2.3. Motion Information Determination Section

The details of the motion information determination section 350 are described below. The motion information determination section 350 determines the motion information reliability based on the image output from the pre-processing section 320, and the motion information output from the motion information acquisition section 340. The motion information reliability indicates whether or not the motion information can be used for the focus control process.

Figure 6:
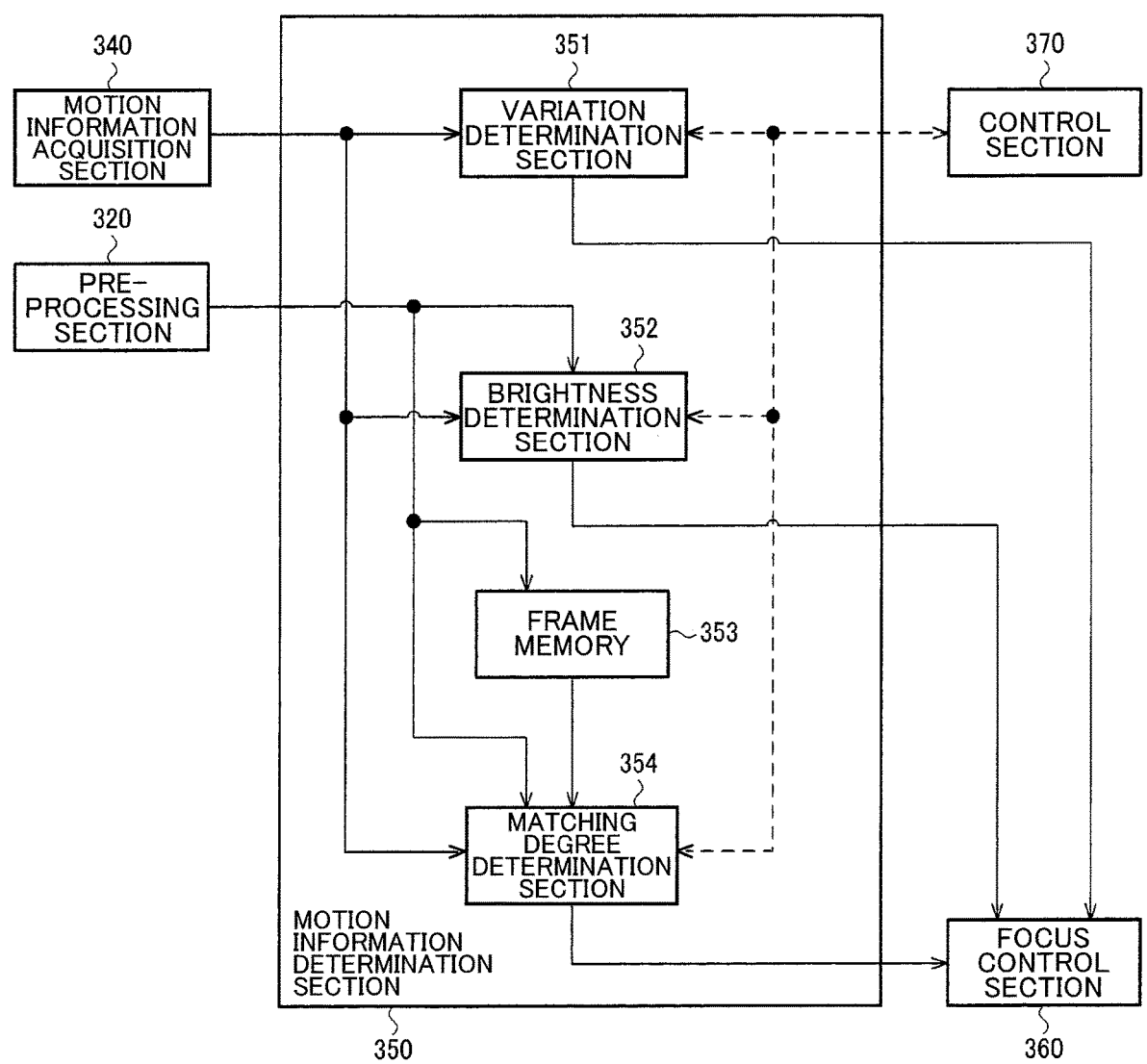
FIG. 6 illustrates a detailed configuration example of a motion information determination section.

FIG. 6 illustrates a detailed configuration example of the motion information determination section 350. The motion information determination section 350 includes a variation determination section 351, a brightness determination section 352, a frame memory 353, and a matching degree determination section 354.

The variation determination section 351 determines whether each motion vector is "reliable" or "unreliable" based on the motion vector output from the motion information acquisition section 340, and outputs the determination result to the focus control section 360. The details of the variation determination section 351 are described later. The brightness determination section 352 determines whether each motion vector is "reliable" or "unreliable" based on the image output from the pre-processing section 320, and outputs the determination result to the focus control section 360. The details of the brightness determination section 352 are described later. The frame memory 353 subjects the image output from the pre-processing section 320 to a frame delay, and outputs the resulting image to the matching degree determination section 354. The matching degree determination section 354 determines whether each motion vector is "reliable" or "unreliable" based on the image output from the pre-processing section 320 (image corresponding to the current frame), the image as a result of the frame delay output from the frame memory 353 (image corresponding to a previous frame), and the motion vector output from the motion information acquisition section 340, and outputs the determination result to the focus control section 360.

The details of the variation determination section 351 are described below. The variation determination section 351 determines the motion information reliability based on spatial similarity of the motion vector output from the motion information acquisition section 340. A motion vector with a high spatial similarity is calculated not based on a noise component but based on a signal component, and thus is determined to be "reliable". The motion information reliability thus determined is output to the focus control section 360.

Figure 7:
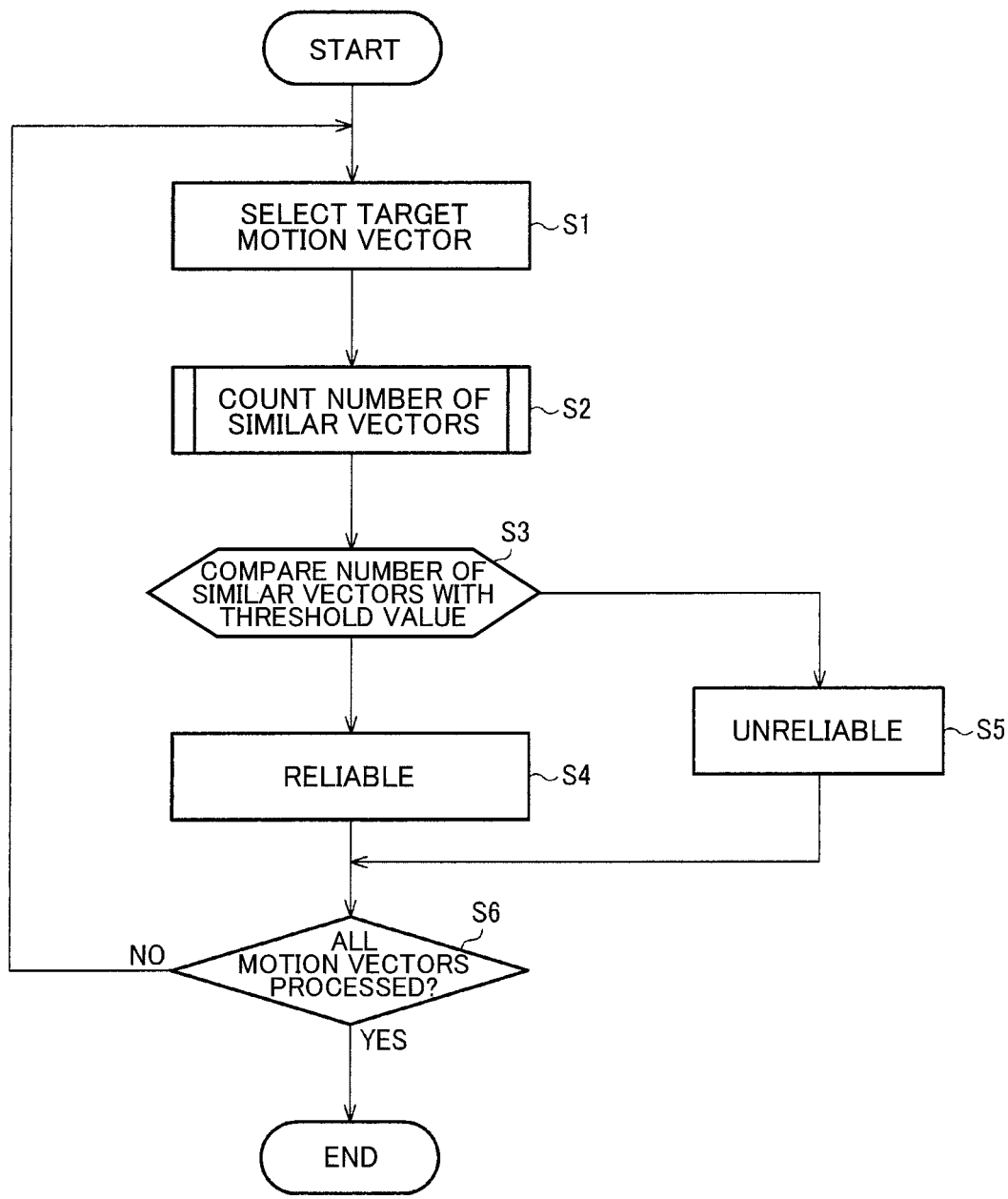
FIG. 7 is a flowchart illustrating a process performed by a variation determination section.

FIG. 7 is a flowchart illustrating the process performed by the variation determination section 351. In the variation determination process, first of all, one of a plurality of local motion vectors in the image (hereinafter, referred to as a target motion vector) is selected (S1). Then, the target motion vector thus selected is subject to a number of similar vectors count process (S2, described in detail later). Then, the number of similar vectors is compared with a predetermined threshold value (S3). The target motion vector with the number of similar vectors exceeding the threshold value has spatial similarity with peripheral motion vectors, and thus is determined to be "reliable" (S4). On the other hand, a target motion vector with the number of similar vectors not exceeding the threshold value is determined to be "unreliable" (S5). Then, whether or not the determination described above has been completed on all of the motion vectors in the image is determined (S6). When the determination has been completed, the variation determination process is terminated. When an undetermined motion vector is remaining, the process returns to step S1, and one undetermined motion vector is selected.

Figure 8:
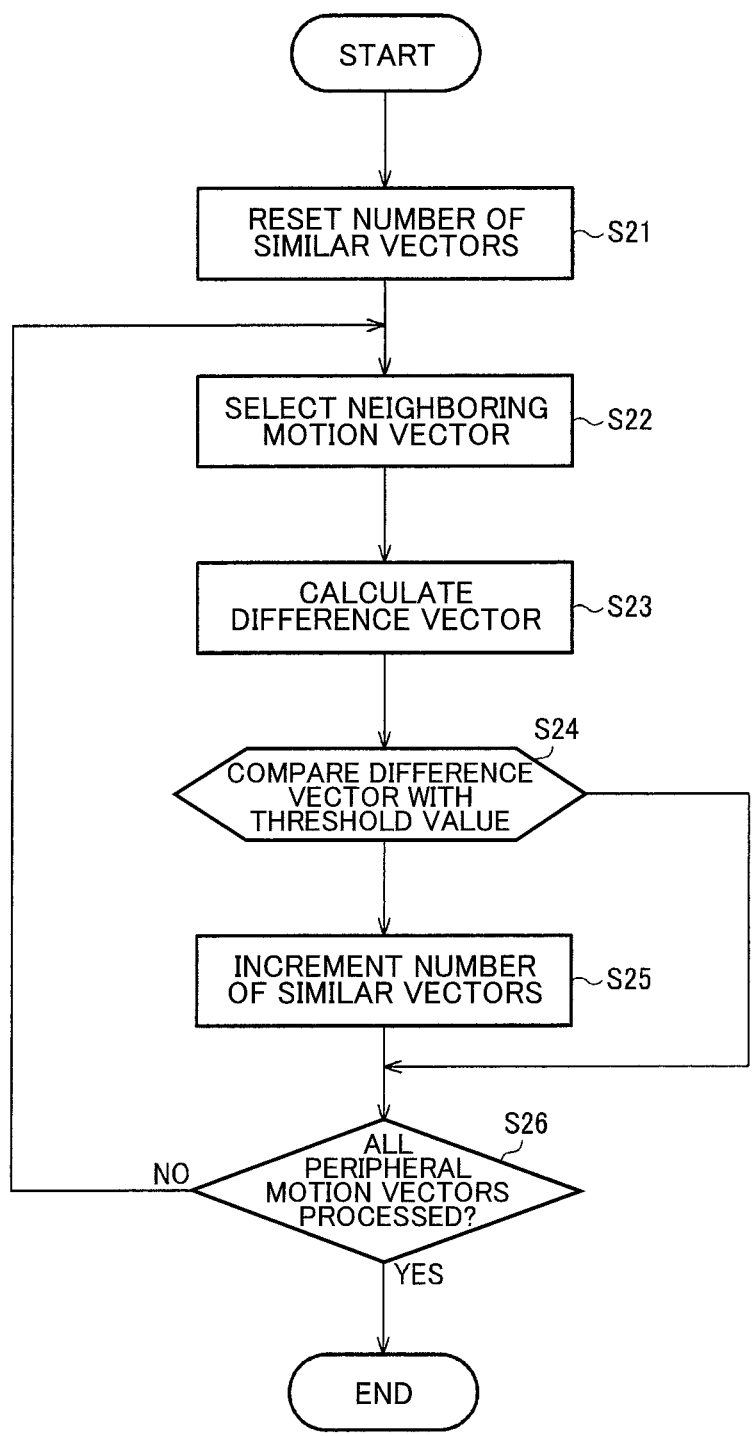
FIG. 8 is a flowchart illustrating a number of similar vectors count process.

FIG. 8 is a flowchart illustrating the number of similar vectors count process (S2). First of all, the number of similar vectors is reset to 0 (S21). Then, one of motion vectors in the periphery of the target motion vector is selected as a neighboring motion vector (S22). For example, the neighboring motion vectors are peripheral motion vectors on upper, lower, left, and right sides of one motion vector in FIG. 5. In step S22, one of the peripheral motion vectors is selected. Next, a difference vector between the target motion vector and the neighboring motion vector is calculated (S23). Next, the magnitude of the difference vector is compared with a predetermined threshold value (S24). When the magnitude of the difference vector does not exceed the threshold value, the number of similar vectors is incremented (S25). When the magnitude of the difference vector exceeds the threshold value, the number of similar vectors remains to be the same. Next, whether or not the determination on a similar vector has been completed for all of the neighboring motion vectors is determined (S26). When the determination has been completed, the number of similar vectors count process is terminated. When there is an undetermined neighboring motion vector, the process returns to step S22, and one undetermined neighboring motion vector is selected.

The details of the brightness determination section 352 are described below. The brightness determination section 352 determines the motion information reliability based on local brightness in the image output from the pre-processing section 320. The motion information reliability is determined to be "unreliable" when the local brightness exceeds a first threshold value (when a pixel value is saturated, when the image is "overexposed". The motion information reliability is determined to be "unreliable" also when the local brightness does not exceed a second threshold value (when the image is underexposed). The motion information reliability is determined to be "reliable" when the local brightness does not exceed the first threshold value and exceeds the second threshold value. The motion information reliability thus determined is output to the focus control section 360.

Figure 9:
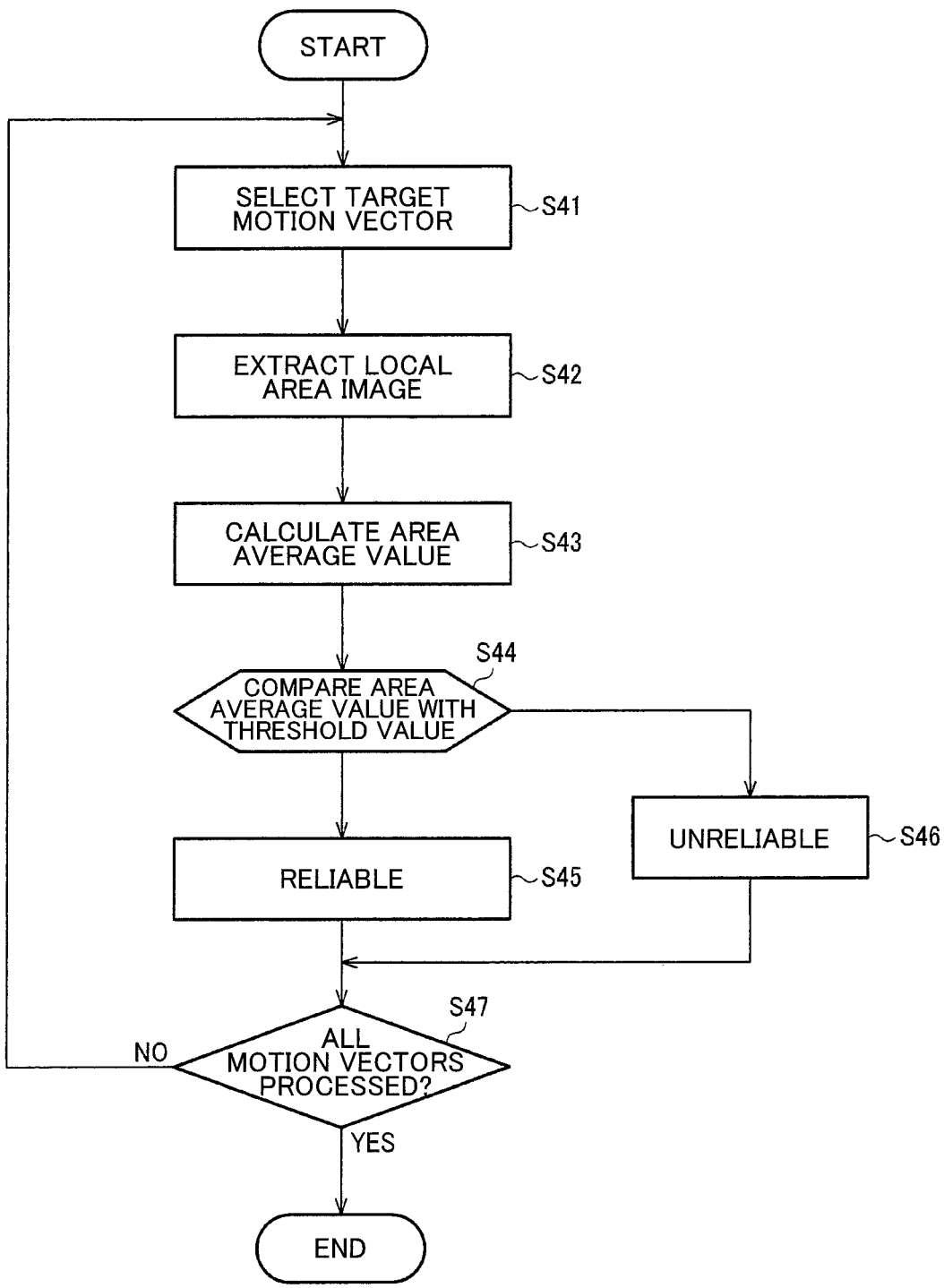
FIG. 9 is a flowchart illustrating a process performed by a brightness determination section.

FIG. 9 is a flowchart illustrating a process performed by the brightness determination section 352. In the brightness determination process, first of all, the target motion vector is selected (S41). Next, an image within a predetermined range around the initial point of the target motion vector is extracted, from the image corresponding to the current frame, as a local area image (S42). For example, the predetermined range, which may be any appropriate range, is a block area used for the block matching for obtaining the target motion vector. Next, a mean value of the brightness in the local area image thus extracted is calculated (S43). For example, a mean value MEAN is calculated by summing up and averaging the G signal values of the local area image. Then, the mean value MEAN thus calculated is compared with the first threshold value TH1 and the second threshold value TH2 (TH1>TH2) (S44). The first threshold value is a value corresponding to overexposed image and the second threshold value is a value corresponding to the underexposed image. When the following Formula (1) is satisfied, the result of the determination is "reliable" (S45). When the following Formula (1) is not satisfied, the result of the determination is "unreliable" (S46).

$$TH1 \geq MEAN > TH2 \qquad (1)$$

Next, whether or not the determination described above has been completed on all the motion vectors in the image is determined (S47). When the determination has been completed, the brightness determination process is terminated. When there is an undetermined motion vector, the process returns to step S41, and one undetermined motion vectors is selected.

The details of the matching degree determination section 354 are described below. The matching degree determination section 354 determines the motion information reliability based on local correlation (matching degree) between the image (current frame) output from the pre-processing section 320 and the image (previous frame) subjected to the frame delay output from the frame memory 353. A low matching degree indicates a failure in local alignment (motion vector detection) between two images, and thus the determination results in "unreliable". When the matching degree is high, the determination results in "reliable". The motion information output from the motion information acquisition section 340 is a result of the local alignment, and thus whether or not the local alignment is reliable is determined based on the correlation between local areas in two images associated with each other by the motion information. The motion information reliability thus determined is output to the focus control section 360.

Figure 10:
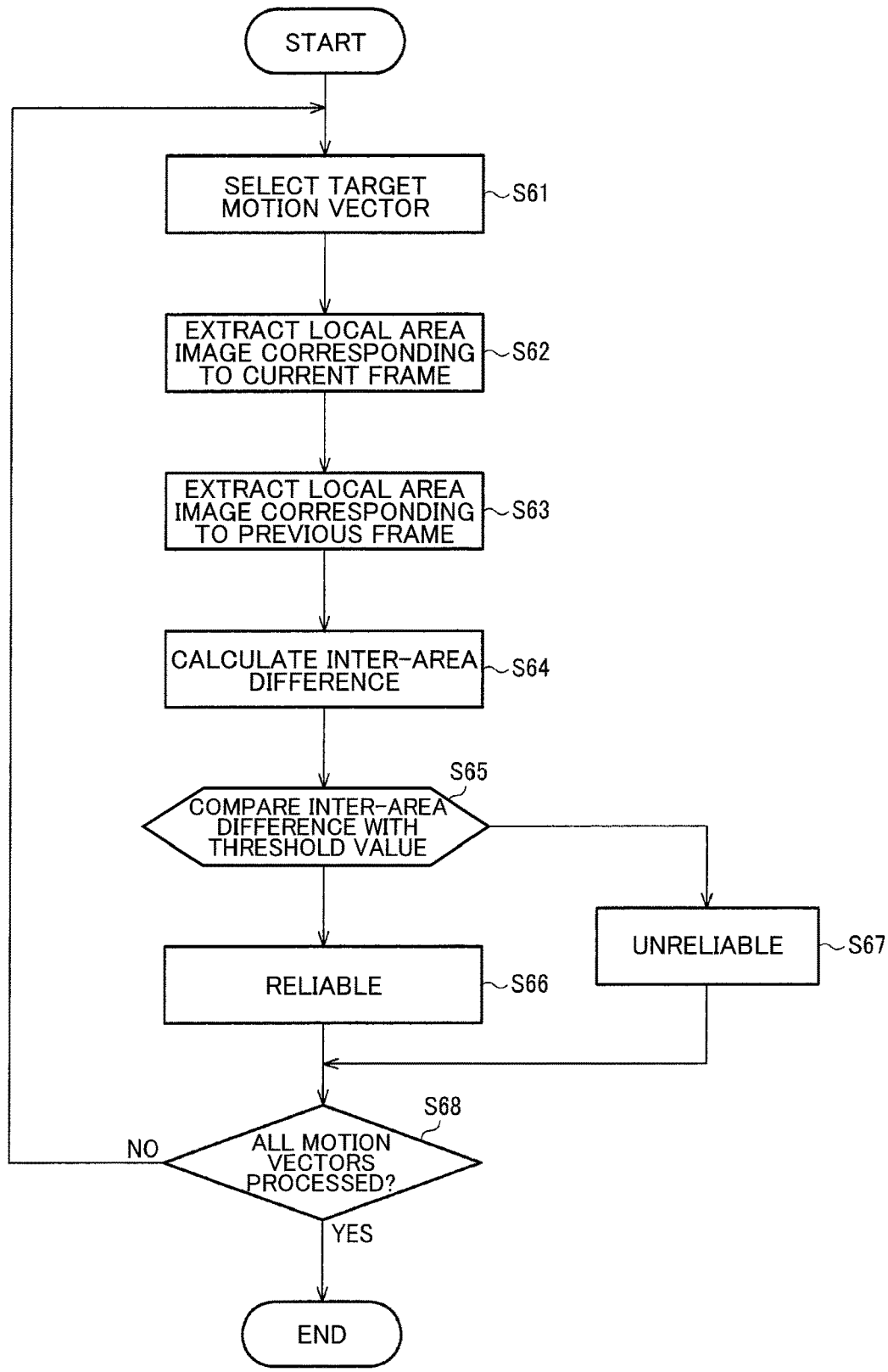
FIG. 10 is a flowchart illustrating a process performed by a matching degree determination section.

FIG. 10 is a flowchart illustrating a process performed by the matching degree determination section 354. In the matching degree determination process, first of all, the target motion vector is selected (S61). Next, an image within a predetermined range around the initial point of the target motion vector is extracted, from the image corresponding to the current frame, as the local area image (S62). For example, the predetermined range, which may be any appropriate range, is a block area used for the block matching for obtaining the target motion vector. Next, an image within a predetermined range around the terminal point of the target motion vector is extracted, from the image corresponding to the previous frame, as a local area image (S63). This predetermined range has the same size as the predetermined range used in step S62. Next, an inter-area difference SUB between a local area image CURR corresponding to the current frame as described above and a local area image PREV corresponding to the previous frame is calculated with the following Formula (2) (S64).

$$SUB = \sum_{j=0}^{J-1} \sum_{i=0}^{I-1} |CURR(i, j) - PREV(i, j)| \qquad (2)$$

Note that I and J are the numbers of pixels in the horizontal and vertical direction in the local area image corresponding to the current frame and the local area image corresponding to the previous frame.

Next, the inter-area difference thus calculated is compared with a threshold value (S65). When the inter-area difference does not exceed the threshold value, the determination result is "reliable" (S66). When the inter-area difference exceeds the threshold value, the determination result is "unreliable" (S67). Next, whether or not the determination described above has been completed on all the motion vectors in the image is determined (S68). When the determination has been completed, the matching degree determination process is terminated. When there is an undetermined motion vector, the process returns to step S61, and one undetermined motion vector is selected.

In the present embodiment, the motion information determination section 350 outputs the motion information reliability, based on logical AND ("reliable" corresponding to TRUE and "unreliable" corresponding to FALSE) between the three determination results, to the focus control section 360. For example, "reliable" is represented by a bit "1", and "unreliable" is represented by a bit "0". The logical AND is "0" if any one of the three determination results is "unreliable", and thus the determination result "unreliable" is output to the focus control section 360. As described above, the local motion vectors are obtained at a plurality of points in an image (FIG. 5 for example), and "reliable"/"unreliable" is determined for each of the motion vectors. Thus, the motion information reliability is information as a result of associating the determination result "reliable/unreliable" with each motion vector.

In the example described above, the motion information reliability is the logical AND of the three determination results. However, this should not be construed in a limiting sense. For example, the motion information reliability may be a single determination result, or may be the logical AND of any two of the determination results. Alternatively, other types of determination may be made and combined.

As described above, the motion information acquisition section 340 obtains the motion information that is a plurality of local motion amounts (e.g., the motion vectors VE), based on a captured image that is an image of an object captured by the imaging section 200. The motion information determination section 350 determines the motion information reliability (for example, "reliable" or "unreliable") for each of the plurality of local motion amounts.

With the reliability of the motion information thus determined, movement of the treatment tool only, motion information erroneously detected due to noise, or the like can be determined as motion information with low reliability. Thus, the focus operation can be performed for a change of scene requiring the AF process, such as movement of the imaging range of the tissue or movement by which the tissue or the treatment tool lies outside the depth of field, with influence of the motion information with low reliability reduced.

In the present embodiment, the motion information determination section 350 determines the motion information reliability based on the correlation between each local motion amount and the peripheral local motion amounts The correlation between each local motion amount and the peripheral local motion amounts is correlation (similarity) between local motion amounts in the magnitude and direction. Specifically, the correlation between local motion amounts close to each other in the magnitude or the direction is high. For example, in the present embodiment, the correlation is determined to be high (thus the determination result is "reliable") when the difference between a motion vector and a peripheral motion vector does not exceed the threshold value.

High correlation relative to peripheral local motion vectors indicates that an object at the corresponding position is moving with a magnitude and direction similar to those of the periphery, and thus the movement can be determined not to be random movement of a treatment tool or the like, noise, or the like. With the local motion amount that is likely to represent the movement of the tissue (background) determined to be highly reliable, a change in scene requiring the AF process can be accurately detected.

In the present embodiment, the motion information determination section 350 determines the motion information reliability based on the brightness of the captured image (for example, a mean luminance value or a mean G pixel value) in areas corresponding to local motion amounts.

The brightness of the captured image in an area corresponding to each local motion amount is brightness of the image in an area where a motion represented by the local motion amount is occurring, or is brightness of the image in an area (e.g., a block area in the block matching) as a target of the process for obtaining the local motion amount.

In the present embodiment, the brightness of the captured image in an area corresponding to each local motion amount is compared with a threshold value, to determine the reliability. Thus, the reliability of the local motion amount in an area where accurate detection of the motion amount cannot be expected can be determined to be low. For example, the determination is made with the threshold values corresponding to overexposure and underexposure. Thus, the reliability of the motion vector corresponding to an area where edge components are disturbed and thus the matching is difficult can be determined to be low.

In the present embodiment, each local motion amount is a motion vector. The motion information determination section 350 determines the motion information reliability based on correlation between a pixel value of one pixel or more corresponding to the initial point of the motion vector and a pixel value of one pixel or more corresponding to the terminal point of the motion vector.

For example, in the present embodiment, the reliability is determined based on the correlation between a block area corresponding to the initial point of the motion vector in an image corresponding to the current frame and a block area corresponding to the terminal point of the motion vector in an image corresponding to a previous frame. These block areas are areas determined to match (determined as the same area of the object) in the block matching. However, this should not be limited sense, and the size of the area may be a single pixel or any other appropriate sizes. The correlation between pixel values indicates similarity between the pixel values, and various correlation coefficient (such as Sum of Absolute Difference (SAD) or Sum of Squared Difference (SSD) for example) may be used.

As described above, the reliability of the matching process can be determined based on the correlation between pixel values of a single pixel or more corresponding to the initial point and the terminal point of a motion vector. Thus, the matching process is merely a process of searching the positions with the highest similarity in a search range, and thus the positions do not necessarily correspond to images of the same object (the position might correspond to areas that happen to be similar to each other). In the present embodiment, the reliability of a motion vector in such a case where the reliability of the matching process is low can be determined to be low.

2.4. Focus Control Section

The details of the focus control section 360 are described below. The focus control section 360 controls whether or not to perform the focus operation (transition from the standby state to the focus operation) based on the motion information output from the motion information acquisition section 340 and the motion information reliability output from the motion information determination section 350. The details of the focus operation are described later.

Figure 11:
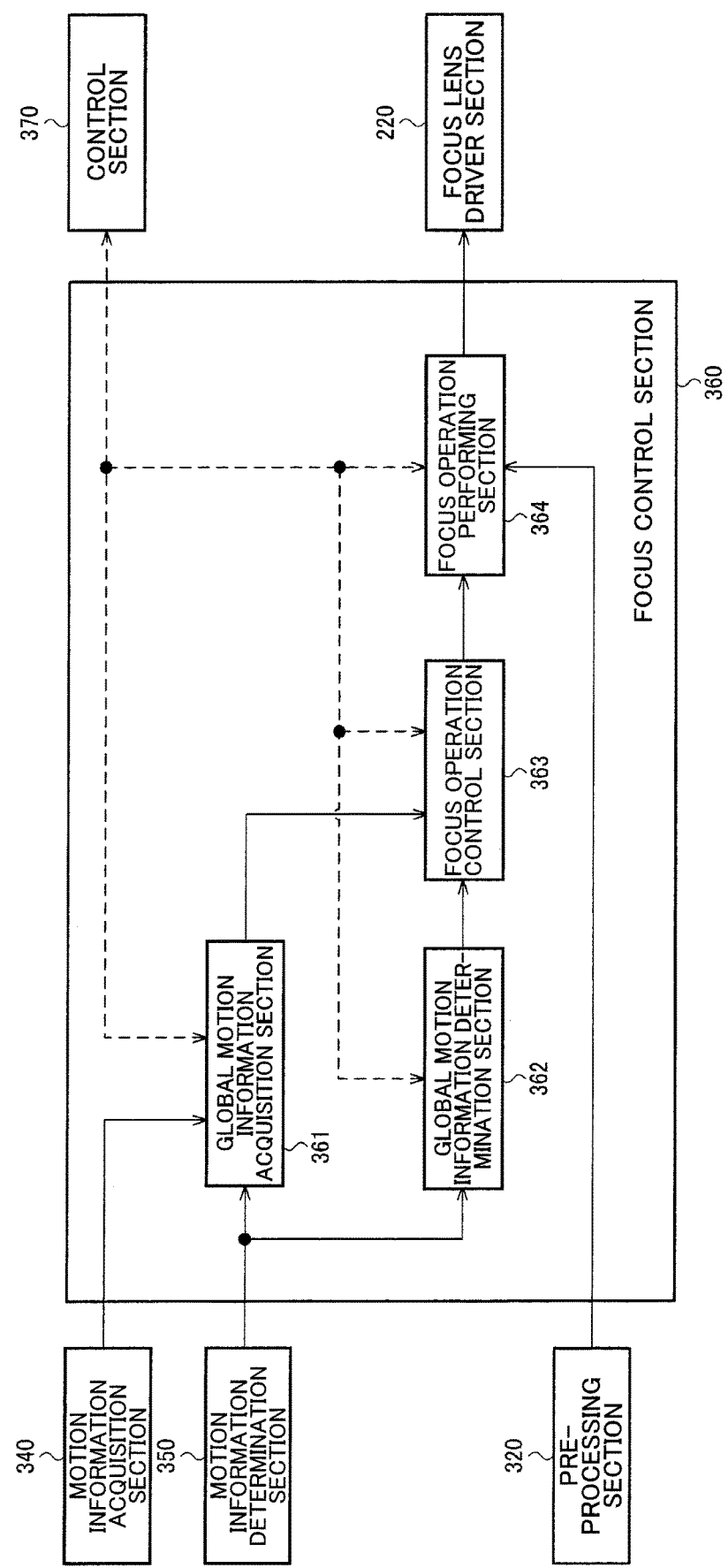
FIG. 11 illustrates a detailed configuration example of a focus control section.

FIG. 11 illustrates a detailed configuration example of the focus control section 360. The focus control section 360 includes a global motion information acquisition section 361, a global motion information determination section 362, a focus operation control section 363, and a focus operation performing section 364.

The global motion information acquisition section 361 acquires the global motion information based on the motion information output from the motion information acquisition section 340 and the motion information reliability output from the motion information determination section 350. The global motion information is information about a motion of the object over the entire image (about the motion in a more global area than a motion vector representing the motion in a local area). The global motion information thus acquired is output to the global motion information determination section 362 and the focus operation control section 363. The details of the global motion information acquisition section 361 are described later.

The global motion information determination section 362 determines the global motion information reliability indicating whether or not the global motion information is effective based on the motion information reliability output from the motion information determination section 350 and the global motion information output from the global motion information acquisition section 361. The global motion information reliability thus determined is output to the focus operation control section 363. The details of the global motion information determination section 362 are described in detail later.

The focus operation control section 363 generates a focus control signal based on the global motion information output from the global motion information acquisition section 361 and the global motion information reliability output from the global motion information determination section 362. The focus control signal is a signal for controlling whether or not to perform the focus operation, and may be turned "ON (to be at a high level for example)" to indicate that "focus operation is to be performed (transition from the standby state to the focus operation)" and turned "OFF (to be at a low level for example)" to indicate that "focus operation is not to be performed (remain in the standby state)". The focus control signal thus generated is output to the focus operation performing section 364. The details of the focus operation control section 363 are described in detail later.

The focus operation performing section 364 performs the focus operation based on an image output from the pre-processing section 320, when the focus control signal output from the focus operation control section 363 is "ON". The focus operation performing section 364 is connected to the focus lens driver section 220 and controls the focus lens driver section 220 to perform the focus operation. After the focus operation has been completed (after the object is determined to have been brought into focus by the AF process), the focus control signal is turned "OFF". The details of the focus operation performing section 364 are described in detail later.

2.5. Global Motion Information Acquisition Section

The details of the global motion information acquisition section 361 are described below. The global motion information includes: components in parallel with a surface (horizontal and vertical components that are collectively referred to as parallel-to-surface motion amount herein); and components orthogonal to the surface (hereinafter, referred to as an orthogonal-to-surface motion amount).

The parallel-to-surface motion amount is a motion amount representing motion in a direction in parallel with a sensor surface of the image sensor 240 (specifically, the motion amount representing the movement in a direction orthogonal to the optical axis of the objective lens system 230). This movement occurs due to the rotation of the scope (rotation about a direction not in parallel with the optical axis) or a parallel movement of the scope (parallel movement in direction not in parallel with the optical axis). Thus, the parallel-to-surface motion amount is a motion amount corresponding to the movement of the imaging range with respect to the object due to the movement of the scope.

The orthogonal-to-surface motion amount is a motion amount representing movement in a direction orthogonal to the sensor surface of the image sensor 240 (specifically, the motion amount representing the movement in a direction in parallel with the optical axis of the objective lens system 230). This movement occurs due to the parallel movement of the scope (parallel movement in a direction in parallel with the optical axis). Thus, the parallel-to-surface motion amount is a motion amount as a result of enlargement or reduction of the imaging range of an object due to the movement of the scope. Generally, the parallel-to-surface motion amount and the orthogonal-to-surface motion amount coexist.

Figure 12:
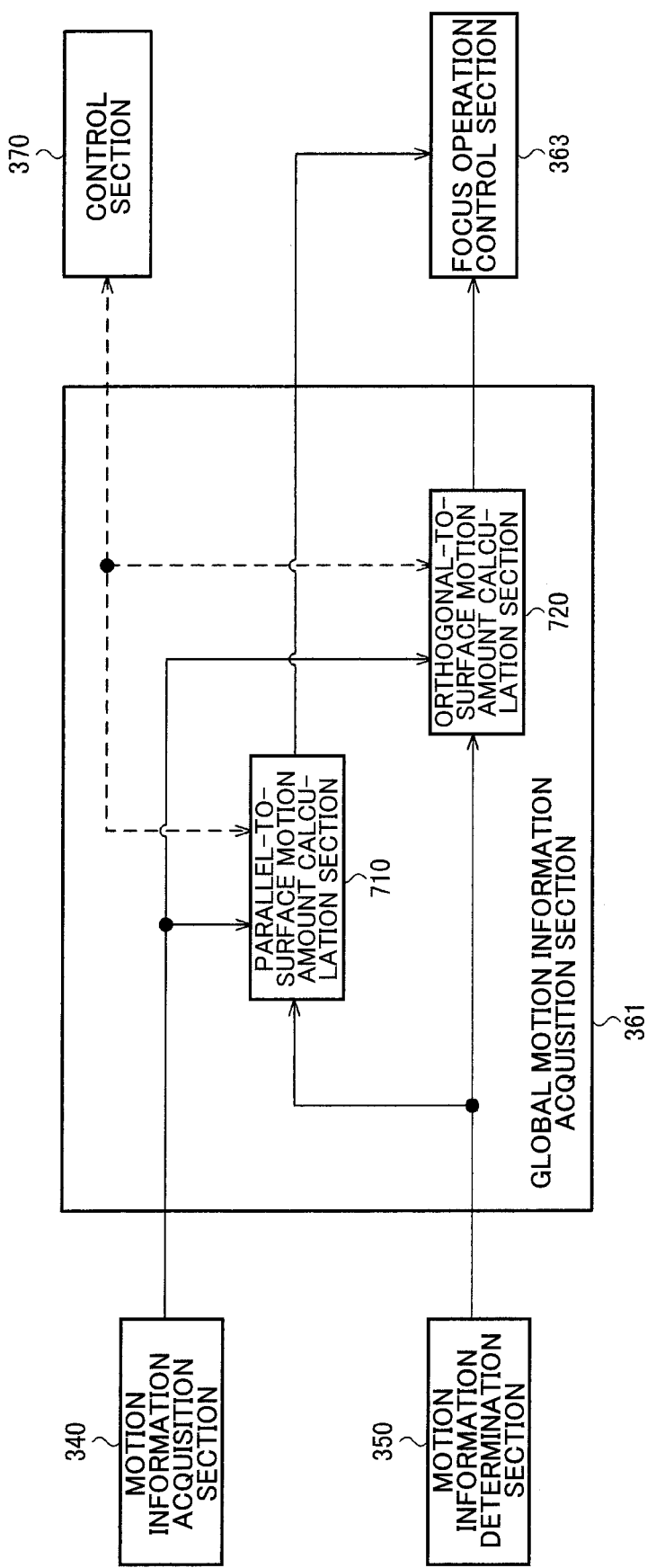
FIG. 12 illustrates a detailed configuration example of a global motion information acquisition section.

FIG. 12 illustrates a detailed configuration example of the global motion information acquisition section 361. The global motion information acquisition section 361 includes a parallel-to-surface motion amount calculation section 710 and an orthogonal-to-surface motion amount calculation section 720.

The parallel-to-surface motion amount calculation section 710 calculates the parallel-to-surface motion amount based on the motion information output from the motion information acquisition section 340 and the motion information output from the motion information determination section 350. The parallel-to-surface motion amount thus calculated is output to the focus operation control section 363. The orthogonal-to-surface motion amount calculation section 720 calculates the orthogonal-to-surface motion amount based on the motion information output from the motion information acquisition section 340 and the motion information reliability output from the motion information determination section 350. The orthogonal-to-surface motion amount thus calculated is output to the focus operation control section 363.

The parallel-to-surface motion amount calculation section 710 calculates the parallel-to-surface motion amount based on motion information, in motion information output from the motion information acquisition section 340, with the motion information reliability, output from the motion information determination section 350, determined to be "reliable".

Figure 13:
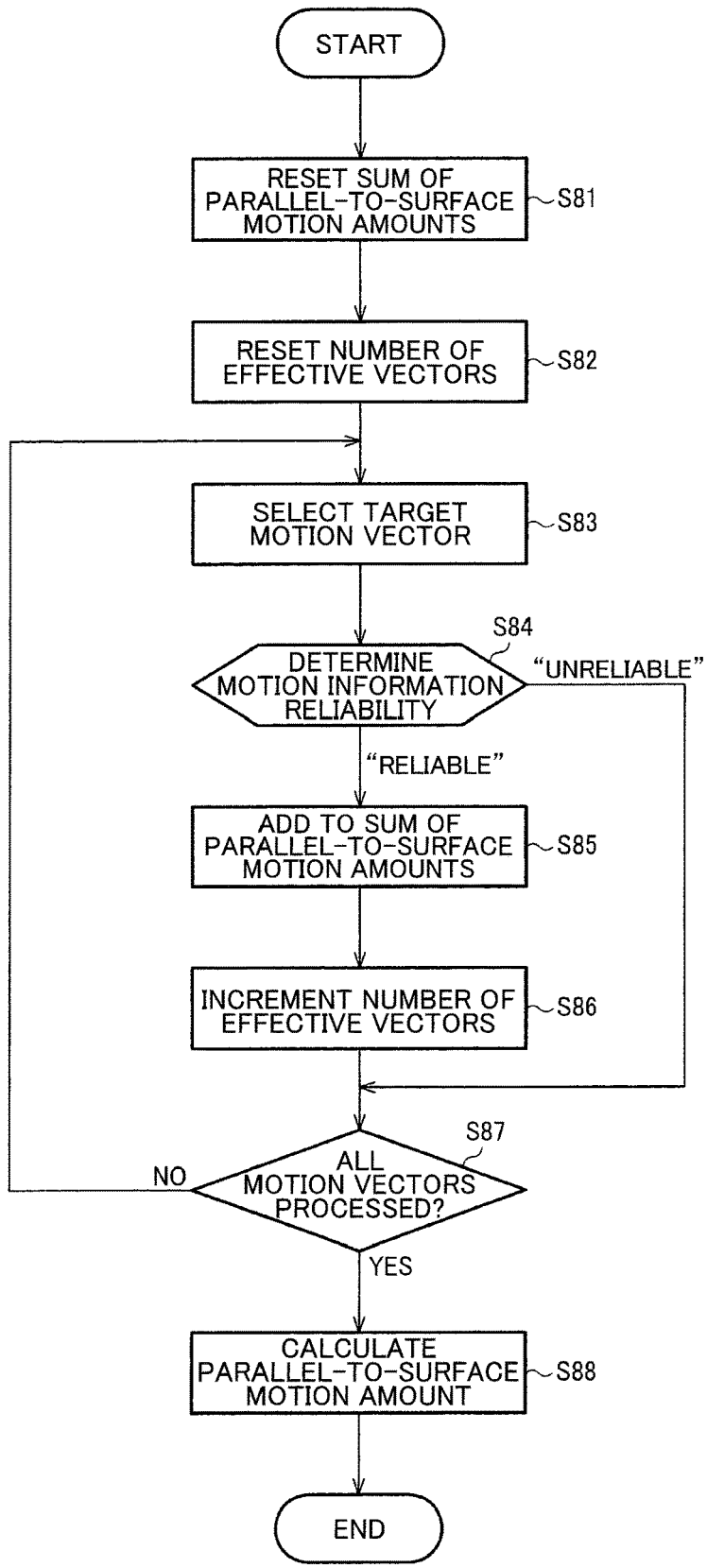
FIG. 13 is a flowchart illustrating a process performed by a parallel-to-surface motion amount calculation section.

FIG. 13 is a flowchart illustrating a process performed by the parallel-to-surface motion amount calculation section 710. First of all, the parallel-to-surface motion amount calculation section 710 resets the sum of the parallel-to-surface motion amounts to 0 vectors (S81). Then, the number of effective vectors is reset to 0 (S82). Then, a target motion vector is selected (S83). Then, whether or not the motion information reliability of the target motion vector thus selected is "reliable" or "unreliable" is determined (S84). When the result of the determination is "reliable", the target motion vector is added to the sum of parallel-to-surface motion amounts (S85) and the number of effective motion vectors is incremented (S86). When the result of the determination is "unreliable", step S85 and step S86 are skipped. Then, whether or not the process described above has been completed on all of the motion vectors in the image is determined (S87). When the process has been completed, the sum of the parallel-to-surface motion amounts is divided by the number of effective motion vectors to calculate the parallel-to-surface motion amount (S88), and the process is terminated. When there is an undetermined motion vector, the process returns to step S83, and one unprocessed motion vector is selected.

The orthogonal-to-surface motion amount calculation section 720 calculates the orthogonal-to-surface motion amount based on motion information, in motion information output from the motion information acquisition section 340, with the motion information reliability, output from the motion information determination section 350, determined to be "reliable". The object on the image is enlarged when the camera moves close to the object, and is reduced when the camera moves away from the object. These movements are calculated based on a change in area between an area including the initial point of the motion vector (corresponding to the object in the current frame, hereinafter referred to as a current object area) and an area including the terminal point of the motion vector (corresponding to the object in the previous frame, hereinafter referred to as a previous object area). The current object area and the previous object area each have a polygonal shape, and have an apex being a part of the motion vector initial point or a part of the motion vector terminal point.

Figure 14:
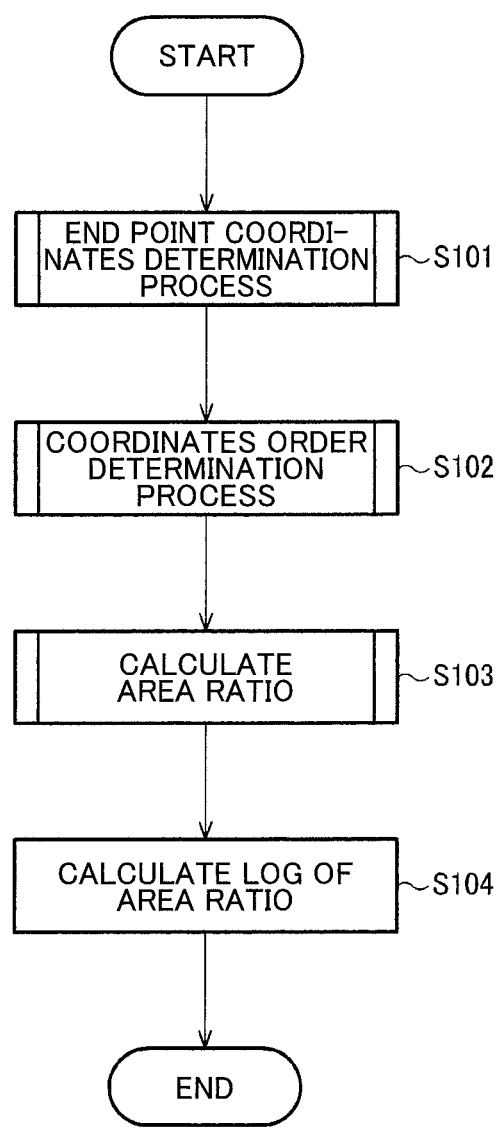
FIG. 14 is a flowchart illustrating a process performed by an orthogonal-to-surface motion amount calculation section.
Figure 15:
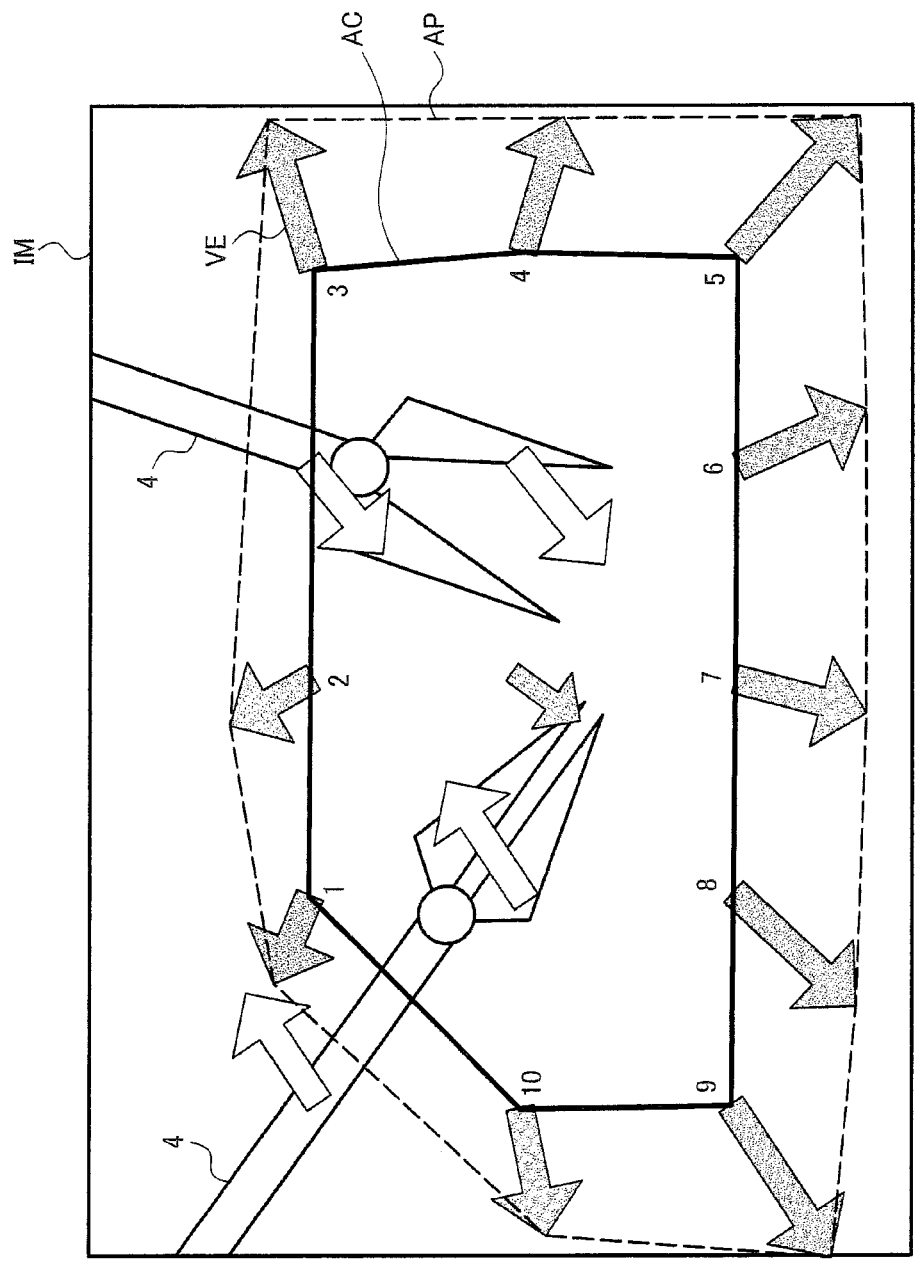
FIG. 15 is a diagram illustrating the process.

FIG. 14 is a flowchart illustrating a process performed by the orthogonal-to-surface motion amount calculation section 720. FIG. 15 is a diagram illustrating the process. A hatched arrow represents a motion vector VE determined to be "reliable", and a white arrow represents a motion vector VE determined to be "unreliable".

First of all, the orthogonal-to-surface motion amount calculation section 720 determines end point coordinates of the apex of the current object area AC (S101). The end point coordinates are coordinates of the initial point of the motion vector VE determined to be "reliable" in the image IM. The details of the end point coordinates determination process S101 are described later in detail. Then, the order of the coordinates is determined to be clockwise relative to the end point coordinates (S102). In FIG. 15, the numbers given to the initial points of the motion vectors VE represent the order. The details of the coordinate order determination process S102 are described later. A ratio between the area of the current object area AC and the area of the previous object area AP (the area of the current object area AC/the area of the previous object area AP) is calculated based on the end point coordinates (the initial points of the motion vectors), the corresponding terminal points of the motion vectors, and the order (S103). The details of the area ratio calculation process S103 are described later. Then, a log of the area ratio is calculated to be the orthogonal-to-surface motion amount (S104). When the camera moves toward the object, the area of the current object area AC>the area of the previous object area AP holds true, and thus the area ratio>1 holds true. Thus, the orthogonal-to-surface motion amount of a positive value is obtained. When the camera moves away from the object as in the example illustrated in FIG. 15, the area of the current object area AC<the area of the previous object area AP holds true, and thus the area ratio<1 holds true. Thus, the orthogonal-to-surface motion amount of a negative value is obtained.

The details of the end point coordinates determination process S101 are described below. In this process, the coordinates of the plurality of points forming the apices of the current object area AC are determined based on the coordinates of the initial points of motion vectors VE, in the motion vectors VE, with the motion information reliability, output from the motion information determination section 350, determined to be "reliable".

Figure 16:
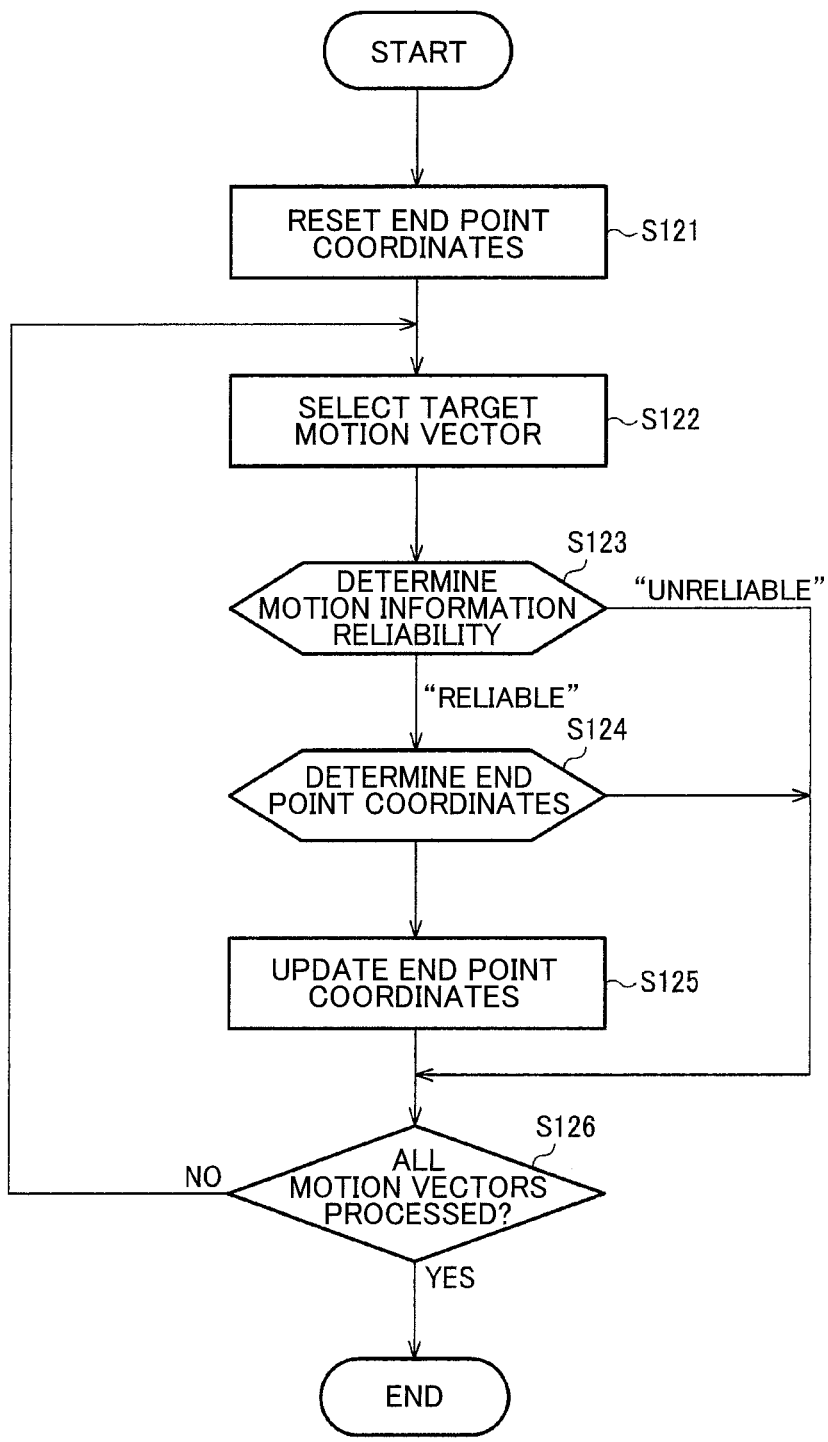
FIG. 16 is a flowchart illustrating an end point coordinates determination process.

FIG. 16 is a flowchart illustrating the end point coordinates determination process S101. First of all, the end point coordinates at the upper end, the lower end, the left end, and the right end are reset (S121). The coordinates thus reset include: the upper end coordinates being the lower end coordinates in the image: the lower end coordinates being the upper end coordinates in the image; the left end coordinates being the right end coordinates in the image; and the right end coordinates being the left end coordinates in the image. Next, a target motion vector is selected (S122). Next, the reliability of the target motion vector is determined (S123). When the target motion vector is "reliable", whether or not the initial point coordinates of the target motion vector are the end point coordinates is determined (S124). For example, whether or not the initial point coordinates are above a current value of the upper end point coordinates, held as a variable, is determined. When the initial point coordinates are above the upper end point coordinates, the initial point coordinates are determined as the upper end point coordinates, and thus the upper end point coordinates are updated (S125). This determination and updating are performed also for the lower end point coordinates, the left end point coordinates, and the right end point coordinates. When the target motion vector is determined to be "unreliable" in step S123, step S124 and step S125 are skipped. Next, whether or not the process described above has been completed for all the motion vectors in the image is determined (S126). When the process has been completed, the process is terminated. When there is an unprocessed motion vector, the process returns to step S122, and one unprocessed motion vector is selected.

The details of the coordinates order determination process S102 are described below. In this process, the order of the apices of the current object area AC is determined based on the upper, lower, left, and right end point coordinates determined in the end point coordinates determination process S101.

Figure 17:
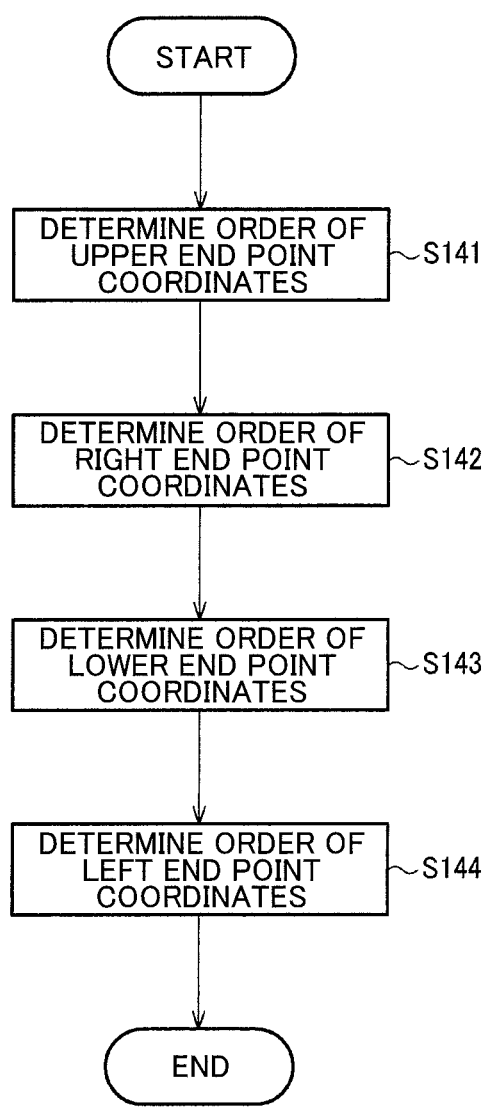
FIG. 17 is a flowchart illustrating a coordinates order determination process.

FIG. 17 is a flowchart illustrating the coordinates order determination process S102. First of all, an initial point with the same coordinates as the upper end point in an upward-downward direction (for example, a vertical scanning direction), in initial vectors of the motion vectors VE determined to be "reliable", is selected. When a plurality of initial points are selected, these points are determined as apices and are numbered in order from the left side to the right side. When a single initial point is selected, the point is determined as the apex, and is numbered (S141). Next, an initial point with the same coordinates as the right end point in a rightward-leftward direction (for example, a horizontal scanning direction), in initial vectors of the motion vectors VE determined to be "reliable", is selected. When a plurality of initial points are selected, these points are determined as apices and are numbered in order from the upper side to the lower side. When a single initial point is selected, the point is determined as the apex, and is numbered (S142). This order continues from the order determined in step S141. Next, an initial point with the same coordinates as the lower end point in the upper and lower direction, in initial vectors of the motion vectors VE determined to be "reliable", is selected. When a plurality of initial points are selected, these points are determined as apices and are numbered in order from the right side to the left side. When a single initial point is selected, the point is determined as the apex, and is numbered (S143). This order continues from the order determined in step S142. Next, an initial point with the same coordinates as the left end point in the left and right direction, in initial vectors of the motion vectors VE determined to be "reliable", is selected. When a plurality of initial points are selected, these points are determined as apices and are numbered in order from the lower side to the upper side. When a single initial point is selected, the point is determined as the apex, and is numbered (S144). This order continues from the order determined in step S143.

The details of the area ratio calculation process S103 are described later. In this process, an area rate S_rate between the polygonal shape (current object area AC) formed of the initial points of the motion vectors determined in the end point coordinates determination process S101 and the polygonal shape (previous object area AP) formed of the corresponding terminal points of the motion vectors, is calculated based on the order determined in the coordinates order determination process S102. Specifically, the calculation is performed through the following Formulae (3) to (5).

$$S\_rate = \frac{S\_curr}{S\_prev} \quad (3)$$

$$S\_curr = \frac{1}{2}\left|\sum_{i=0}^{N} (x\_curr_i - x\_curr_{i+1}) \times (y\_curr_i + y\_curr_{i+1})\right| \quad (4)$$

$$S\_prev = \frac{1}{2}\left|\sum_{i=0}^{N} (x\_prev_i - x\_prev_{i+1}) \times (y\_prev_i + y\_prev_{i+1})\right| \quad (5)$$

Note that S_curr is the area of the current object area AC. S_prev is the area of the previous object area AP. (x_curri, y_curri) is the apex coordinates (initial point of the motion vector) of the current object area AC determined in the end point coordinates determination process S101. The reference sign "i" indicates the order of the coordinates determined in the coordinates order determination process S102 and is an integer satisfying 0≤i≤N (note that i=0 and i=N indicate the same apex because the current object area AC has a polygonal shape), and (x_previ,y_previ) is the coordinates (terminal point of the motion vector) of the apex coordinates of the previous object area AP. The order is set to be the same as that of the current object area AC so that (x_curri,y_curri) and (x_previ,y_previ) correspond to the initial point and the terminal point of a single motion vector.

When the global motion information (the parallel-to-surface motion amount and the orthogonal-to-surface motion amount) is acquired based on the motion vector determined to be reliable as described above, the movement of the entire image can be acquired with robustness against noise and local motions ensured (that is, with the influence of the noise and local motions reduced). For example, a local motion of an object that may occur when a medical endoscope is used includes pulsation, a movement of a treatment tool, and the like.

The orthogonal-to-surface motion amount calculation section 720 may obtain the orthogonal-to-surface motion amount through a process according to the following modification.

Specifically, the orthogonal-to-surface motion amount calculation section 720 calculates the orthogonal-to-surface motion amount from a coordinate conversion parameter for the initial point coordinates and the terminal point coordinates of the motion vector determined to be "reliable" (the following Formula (6)). Here, the coordinate conversion is Helmert conversion. Thus, one coordinate is converted to another coordinate through the Helmert conversion.

$$\begin{pmatrix} X \\ Y \\ 1 \end{pmatrix} = \begin{pmatrix} a & -b & c \\ b & a & d \\ 0 & 0 & 1 \end{pmatrix} \begin{pmatrix} x \\ y \\ 1 \end{pmatrix} \quad (6)$$

Note that (x,y) is coordinates before conversion, (X,Y) is coordinates after the conversion, and a, b, c, d are Helmert conversion coefficients. For all the motion vectors determined to be reliable, the terminal point coordinates are set to be the coordinates before the conversion (x,y) and the initial point coordinates are set to be the coordinates after the conversion (X,Y). Then, Helmert conversion coefficients achieving the minimum error in the Helmert conversion for the coordinates are calculated through a least squares method. The Helmert conversion coefficients a and b thus calculated are coefficients related to a magnification change of the coordinates and to rotation of the coordinates. This magnification change D_change can be calculated as in the following Formula (7).

$$D\_change = \sqrt{a^2 + b^2} \quad (7)$$

The magnification change D_change corresponds to the area ratio S_rate described above with reference to Formula (3). Thus, a log of the magnification change D_change is similarly obtained as the orthogonal-to-surface motion amount. When the camera moves close to the object, the magnification change≥1.0 holds true, and thus the orthogonal-to-surface motion amount of a positive value is obtained. When the camera moves away from the object, the magnification change≤1.0 holds true, and thus the orthogonal-to-surface motion amount of a negative value is obtained.

2.6. Global Motion Information Determination Section

Figure 18:
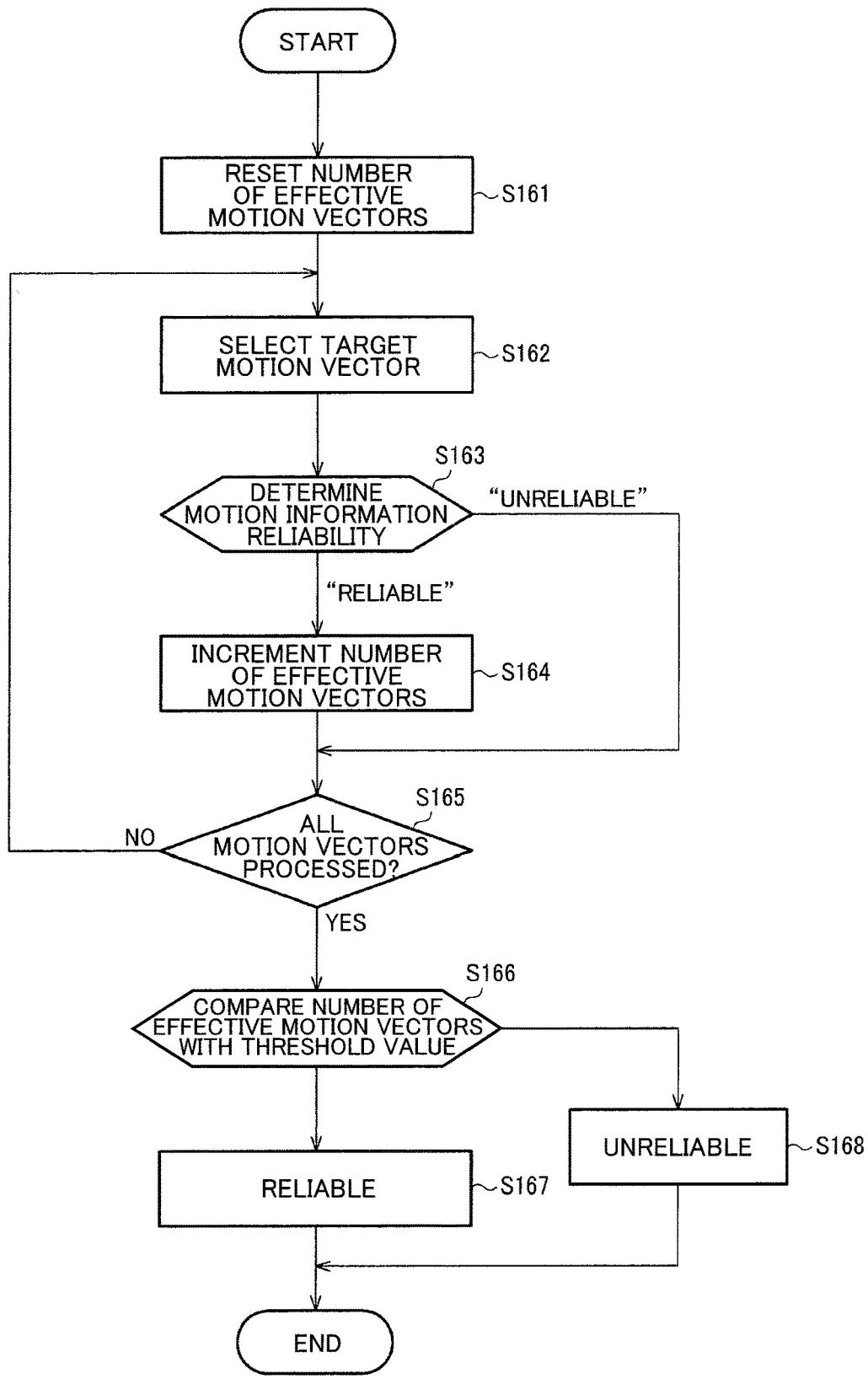
FIG. 18 is a flowchart illustrating a process performed by a global motion information determination section.

The details of the global motion information determination section 362 are described below. FIG. 18 is a flowchart illustrating a process performed by the global motion information determination section 362. First of all, the number of effective motion vectors is reset to 0 (S161). Next, a target motion vector is selected (S162). Next, for the target motion vector thus selected, whether the motion information reliability output from the motion information determination section 350 is "reliable" or "unreliable" is determined (S163). When the result of the determination is "reliable", the number of effective motion vectors is incremented (S164). When the result of the determination is "unreliable", the process proceeds to step S165. Next, whether or not step S162 to S164 have been completed on all of the motion vectors in the image is determined (S165). When the process has been completed, the process proceeds to step S166.

When there is an unprocessed motion vector, the process returns to step S162, and one unprocessed motion vector is selected. In step S166, the number of effective motion vectors is compared with a threshold value (S166). When the number of effective motion vectors exceeds the threshold value, the global motion information is determined to be "reliable" (S167). When the number of effective motion vectors does not exceed the threshold value, the global motion information is determined to be "unreliable" (S168).

2.7. Focus Operation Control Section

Figure 19:
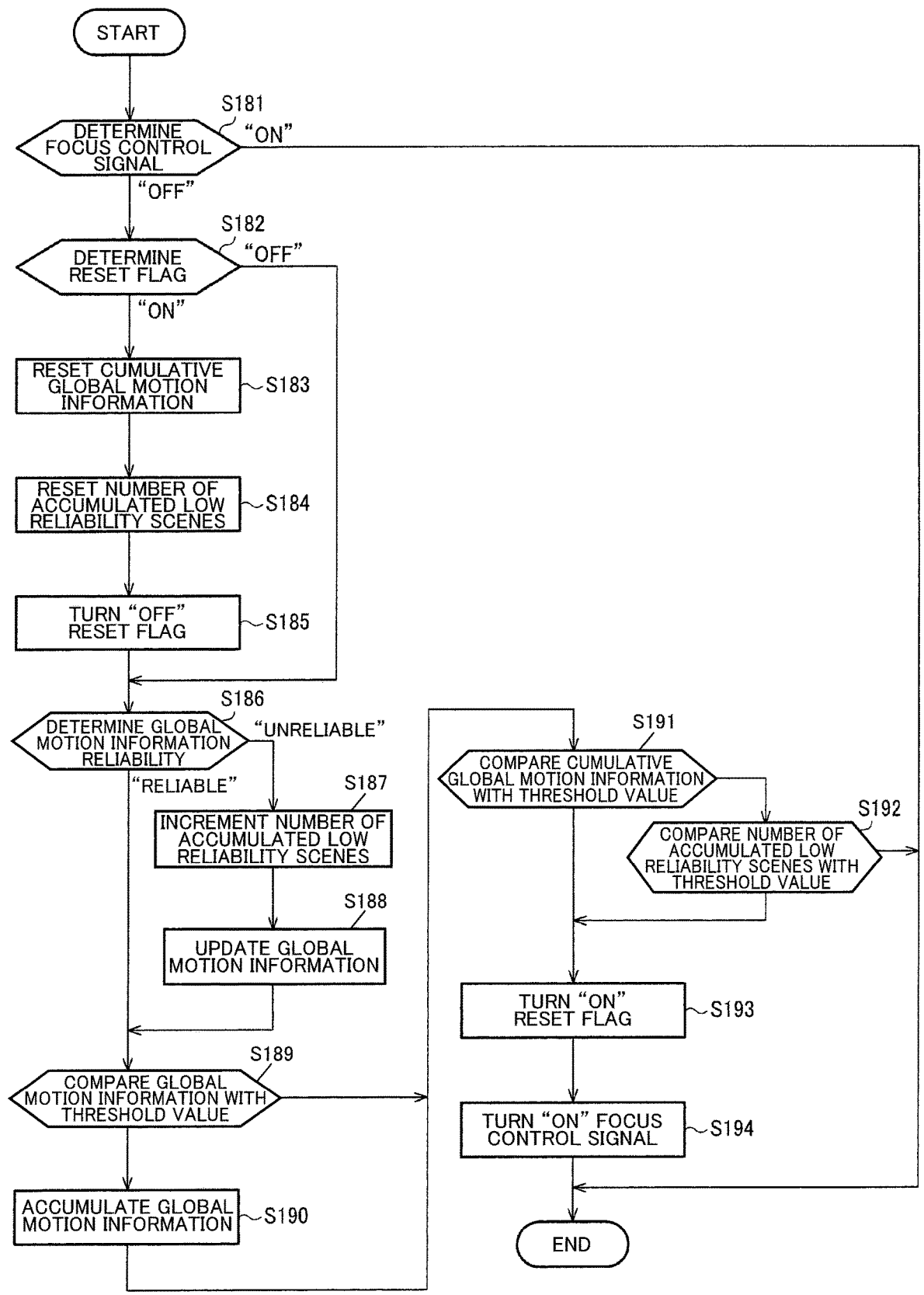
FIG. 19 is a flowchart illustrating a process performed by a focus operation control section.

The details of the focus operation control section 363 are described below. FIG. 19 is a flowchart illustrating a process performed by the focus operation control section 363. First of all, whether the focus control signal is "ON" or "OFF" is determined (S181). When the focus control signal is "ON", the focus operation control process is terminated. When the focus control signal is "OFF", whether a reset flag is "ON" or "OFF" is determined (S182). When the reset flag is "ON", the cumulative global motion information is reset to 0 vectors (S183), the number of accumulated low reliability scenes is reset to 0 (S184), the reset flag is turned "OFF" (S185), and the process proceeds to step S186. When the reset flag is "OFF" in step S182, the process proceeds to step S186. In step S186, whether the global motion information reliability, output from the global motion information determination section 362, is "reliable" or "unreliable" is determined (S186). When a result of the determination is "reliable", the process proceeds to step S189. When a result of the determination is "unreliable", the number of accumulated low reliability scenes is incremented (S187), the global motion information is updated (S188), and the process proceeds to step S189. Step S188 is described later. In step S189, the global motion information is compared with a threshold value. When the global motion information exceeds the threshold value, the global motion information is added to the cumulative global motion information (accumulation) (S190), and the process proceeds to step S191. When the global motion information does not exceed the threshold value, the process proceeds to step S191.

In step S191, the cumulative global motion information is compared with a threshold value. When the cumulative global motion information exceeds the threshold value, the process proceeds to step S193. When the cumulative global motion information does not exceed the threshold value, the number of accumulated low reliability scenes is compared with a threshold value (S192). When the cumulative global motion information exceeds the threshold value, the process proceeds to step S193. When the number of accumulated low reliability scenes does not exceed a threshold value, the focus operation control process is terminated. In step S193, the reset flag is turned "ON", and then, the focus control signal is turned "ON" (S194).

In step S188, the global motion information is updated as follows. Specifically, the global motion information corresponding to the immediately preceding frame (in a wide sense, a frame before the current frame) is copied as the global motion information corresponding to the current frame. In this process, the copying is performed when the global motion information reliability corresponding to the immediately preceding frame is "reliable", and is not performed when the global motion information reliability is "unreliable".

By using immediately preceding motion information with which the detection has been successful ("reliable"), the motion-based focus operation control can be stably performed.

Instead of simply copying the global motion information corresponding to the immediately preceding frame, only the signs of the parallel-to-surface motion amount and the orthogonal-to-surface motion amount may be copied and absolute values thereof may be used as a fixed parameter. With this configuration, the global motion information corresponding to the immediately preceding frame needs not to be held, and thus cost reduction can be achieved.

With the comparison in step S189, small global motion information due to shake or the like can be eliminated as noise, whereby more stable focus operation control can be achieved.

In step S191, the cumulative global motion information, as a result of the process of accumulating the global motion information with the global motion information reliability determined to be "reliable" in step S186, is compared with a threshold value. When the information exceeds the threshold value, the focus operation is determined to be required, and the focus control signal is turned "ON". With the focus operation controlled based on the "reliable" global motion information, more reliable control can be achieved.

2.8. Focus Operation Performing Section

The details of the focus operation performing section 364 are described below. When the focus control signal is "ON", the focus operation performing section 364 drives the focus lens 210 in synchronization with the image output timing based on the image output from the pre-processing section 320 to perform the focus operation.

Figure 20:
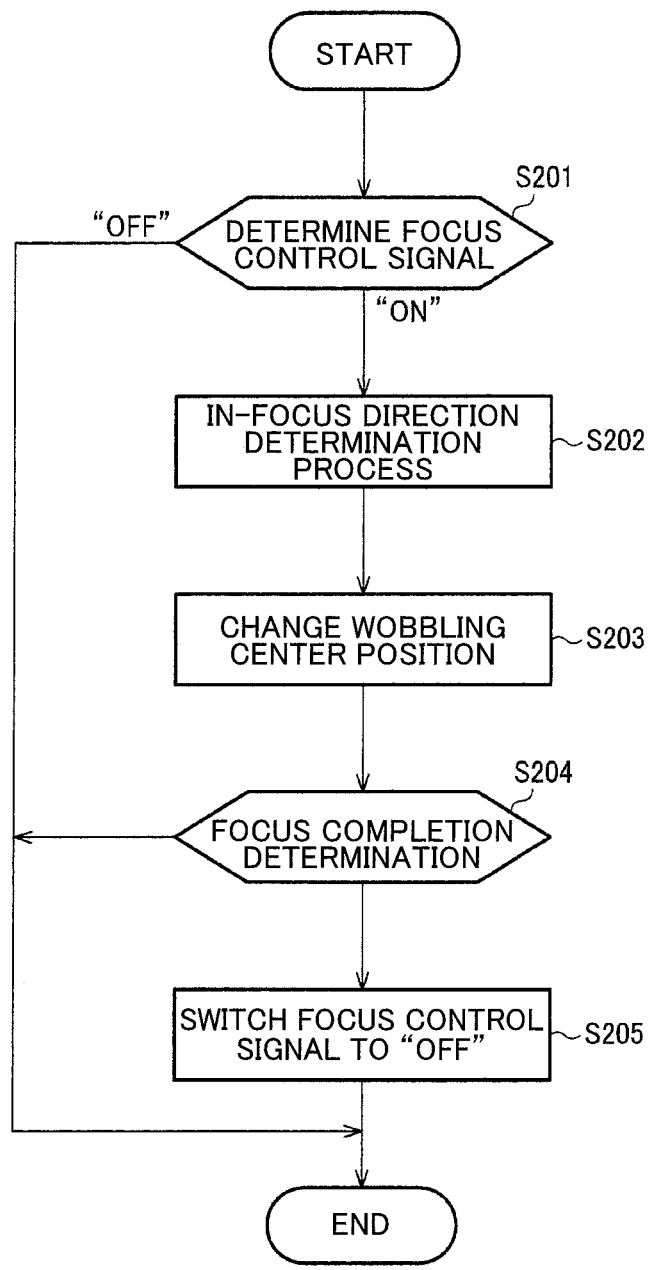
FIG. 20 is a flowchart illustrating a process performed by a focus operation performing section.

FIG. 20 is a flowchart illustrating a process performed by the focus operation performing section 364. First of all, whether the focus control signal is "ON" or "OFF" is determined (S201). When the focus control signal is "ON", the process proceeds to step S202. When the focus control signal is "OFF", the focus operation performing process is terminated. In step S202, an in-focus direction (a direction in which the focus lens 210 is driven at the next image output timing) is determined based on an image output from the pre-processing section 320, through a known method for example. Next, the wobbling center position is changed based on the in-focus direction thus determined (S203), and a wobbling motion is caused at the center position. Specifically, the in-focus direction determined in S203 is a direction in which an in-focus object position is situated on a near side close to the imaging section 200 or a direction in which the in-focus object position is situated on an infinity side far from the imaging section 200. Next, whether or not the focusing has been successfully completed (whether or not the object has been brought into focus) is determined through a known method for example (S204). When the object has been brought into focus, the focus control signal is switched from "ON" to "OFF" (S205), and then the focus operation performing process is terminated. When the object has not been brought into focus, the focus operation performing process is terminated.

When the focus control signal is turned "OFF" with the object determined to have been brought into focus in step S204, the standby state where no AF is performed is achieved, and the process in step S182 and after in the flow illustrated in FIG. 19 is performed. When the cumulative global motion information is determined to be equal to or smaller than the threshold value in step S191, and the number of accumulated low reliability scenes is determined to be equal to or smaller than the threshold value in step S192, the focus control signal remains to be "OFF" and the standby state is maintained. Thus, the processes in step S182 and after are performed again. When the cumulative global motion information is determined to be larger than the threshold value in step S191, or the number of accumulated low reliability scenes is determined to be larger than the threshold value in step S192, the focus control signal is turned "ON" in step S194, and the processes in step S202 and after in FIG. 20 are performed. The processes in step S202 and after are repeated until the object is determined to have been brought into focus in step S204 and the focus control signal is turned "OFF" in step S205. Thus, the focus operation and the standby state are alternately implemented.

As described above, the focus control section 360 obtains the cumulative global motion information as a result of the process of accumulating the global motion information about the global relative motion between the imaging section 200 and the object (for example, the log of the parallel-to-surface motion amount, the orthogonal-to-surface motion amount, and the area ratio obtained in the flows in FIG. 13 and FIG. 14) over a plurality of frames, based on the motion information and the motion information reliability (S186 to S190 in FIG. 19). The focus operation is performed when the cumulative global motion information is determined to be larger than the threshold value for the cumulative global motion information (S191 to S194 in FIG. 19).

With the focus operation performed when the global motion amount accumulated over a plurality of frames exceeds a predetermined amount, the AF control can be implemented in such a manner that the focus operation is performed for motions that are slow accumulated to be a large amount of movement, and is not performed for a momentary motion unintended by the user.

The threshold value for the cumulative global motion information is a threshold value for detecting relative motion, with respect to the imaging section 200 and an object, represented by the cumulative global motion information. Specifically, the global motion information indicates an inter-frame motion amount for example, and is accumulated (summed up or integrated for example) to be the cumulative global motion information. Thus, the cumulative global motion information represents motion in a longer period than the global motion information (represents the movement amount over a plurality of frames). For example, the global motion information corresponds to the speed of a motion, and the movement amount (distance and direction) as a result of integrating this information corresponds to the cumulative global motion information. The determination is made on the cumulative global motion information with a threshold value, and thus a motion amount can be determined. For example, the threshold value may be a value corresponding to ⅓ or ½ of the image size. In this configuration, the focus operation is performed when the object moves by ⅓ or ½ of the image size on the image (that is, when the imaging range moves). Alternatively, the threshold value may be a value corresponding to the depth of field. In this configuration, the focus operation is performed when the object lies outside the depth of field.

In the present embodiment, the focus control section 360 determines the global motion information reliability, indicating the reliability of the global motion information, based on the motion information reliability. For a frame in which the global motion information reliability is determined to be low (for example, "unreliable"), the process of accumulating the global motion information is not performed (process proceeds from S186 to S187 and S188 in FIG. 19).

For example, in the present embodiment, when the global motion information is determined to be "unreliable" in step S186, the global motion information corresponding to the current frame is updated with the global motion information corresponding to the immediately preceding frame in step S188. Thus, the global motion information corresponding to the current frame is not accumulated in step S190. Note that this should not be construed in a limiting sense, and a flow in which step S190 is skipped when the global motion information is determined to be "unreliable" in step S186 may be employed.

When the global motion information corresponding to low frame global motion information reliability is not accumulated, whether or not the focus operation can be determined based on highly reliable global motion information. For example, when the matching process fails due to noise or the like, many local motion vectors might be determined to be "unreliable". With such global motion information determined to have low reliability, influence of global motion information that might not be accurately representing a global motion of the tissue (background) can be reduced.

In the present embodiment, the focus control section 360 does not perform the accumulation process for global motion information corresponding to a frame with the motion amount representing the global motion information determined to be smaller than the threshold value for the global motion information (process proceeds from S189 to S191 in FIG. 19).

Thus, small global motion information generated due to shake or the like for example can be eliminated as noise with the determination using the threshold value. Thus, only relatively large movement, generated when the scope is operated as the user intended, can be detected, whereby whether or not the focus operation is required can be stably determined.

In the present embodiment, the focus control section 360 perform a process in such a manner that for a frame with the global motion information reliability determined to be low, the global motion information in a frame before (immediately preceding frame for example) the current frame is accumulated as the global motion information of the frame (step S188). Alternatively, the focus control section 360 may perform a process in such a manner that for a frame with the global motion information reliability determined to be low, predetermined global motion information is accumulated as the global motion information of the frame.

For example, when a motion is fast, a motion vector might be failed to be detected in the matching process, and thus a result of the determination might be "unreliable". In such a condition, if the cumulative global motion information does not increase, the focus operation might not be performed despite the necessity to perform the focus operation. In view of this, in the present embodiment, the global motion information corresponding to the immediately preceding frame is accumulated so that the cumulative global motion information increases. Thus, failure to perform the focus operation for the movement of the scope can be prevented.

In the present embodiment, the focus control section 360 determines whether or not to perform the focus operation based on the number of frames with the global motion information determined to have low reliability (S187 and S192 in FIG. 19). Specifically, the focus control section 360 performs the focus operation when the number of frames, in a predetermined number of frames, with the global motion information determined to have low reliability exceeds the threshold value for the number of frames (the process proceeds to S193 and S194 from S192). Alternatively, the focus control section 360 may perform the focus operation when the number of frames with the global motion information sequentially determined to have low reliability (the number of frames consecutively determined to have low reliability) exceeds the threshold value for the number of frames.

When the global motion information is frequently determined to have low reliability, a situation in which the reliability of the motion information is low is continuing. Thus, there is no guarantee that the scene has not changed (the same object is being captured). If how such a situation has changed cannot be recognized, the object might be out of focus. Thus, the focus operation is determined to be necessary, whereby a precautionary approach can be employed to bring the object into focus in a situation where the scene cannot be determined.

3. Third Embodiment

Figure 21:
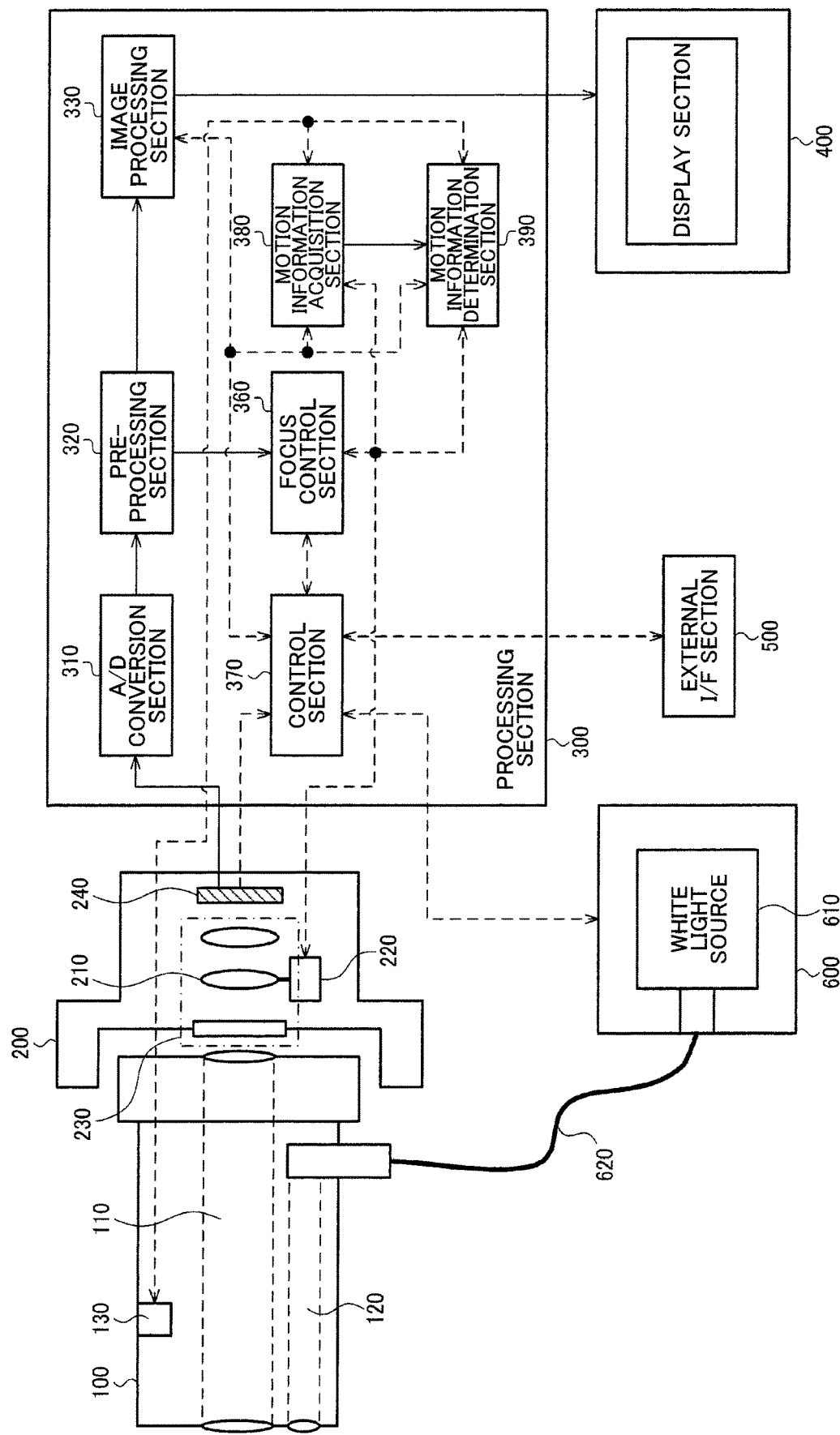
FIG. 21 illustrates a configuration example of an endoscope apparatus (third embodiment).

FIG. 21 illustrates a configuration example of an endoscope apparatus according to a third embodiment. The endoscope apparatus includes a rigid scope 100 that is inserted into a body, an imaging section 200 that is connected to the rigid scope 100, a processing section 300, a display section 400, an external I/F section 500, and a light source section 600. The description of the elements that have been described in the first and the second embodiments is omitted as appropriate.

The rigid scope 100 includes a 6-axis motion sensor 130 that detects triaxial rotational motions and triaxial translational motions. The rigid scope 100 outputs a detection signal (motion signal) from the motion sensor 130 to the processing section 300. For example, the motion sensor 130 includes an angular acceleration sensor (gyro sensor) that detects angular accelerations around three axes (i.e., an x-axis, a y-axis, and a z-axis that are orthogonal to each other), and an acceleration sensor that detects accelerations in triaxial (i.e., x-axis, y-axis, and z-axis) directions. The motion sensor 130 operates at a frequency sufficiently higher than the operating frequency (frame frequency) of the image sensor 240. The motion sensor 130 integrates the detected angular accelerations and accelerations using an integrator (not illustrated in the drawings), and outputs the integration results as a change in angle and a change in position. The integration start/end timing is synchronized with the operation timing (image capture timing) of the image sensor 240. The motion signal represents a change in angle and a change in position of the rigid scope 100 that have occurred between the operation timings (frames) of the image sensor 240.

The processing section 300 includes an A/D conversion section 310, a pre-processing section 320, an image processing section 330, a focus control section 360, a control section 370, a motion information acquisition section 380, and a motion information determination section 390.

The motion information acquisition section 380 acquires the motion information based on a detection signal output from the motion sensor 130 and the in-focus object position. The motion information thus acquired is output to the focus control section 360 and the motion information determination section 390. The motion information includes the parallel-to-surface motion amount and the orthogonal-to-surface motion amount as in the second embodiment.

The parallel-to-surface motion amount is calculated from the parallel-to-surface component (i.e., the yaw component and the pitch component of a change in angle) of a change in position (motion in the real space). More specifically, the parallel-to-surface motion amount is the sum of a term that converts a change in position in the real space into the motion amount within the image based on the imaging magnification, and a term that converts a change in angle in the real space into the motion amount within the image based on the ratio with respect to the maximum angle of view (see the following expressions (8) and (9)).

$$MV\_UD = HEAVE \times ZOOM(P) + PITCH \div MAX\_ANGLE\_UD \times MAX\_PIXEL\_UD \quad (8)$$

$$MV\_LR = SWAY \times ZOOM(P) + YAW \div MAX\_ANGLE\_LR \times MAX\_PIXCEL\_LR \quad (9)$$

Note that HEAVE is a component of the change in position in the upward-downward direction, and SWAY is a component of the change in position in the rightward-leftward direction. ZOOM(P) is the imaging magnification at the object in-focus position P. PITCH is the pitch component of the change in angle, and YAW is the yaw component of the change in angle. MAX_ANGLE_UD is the maximum angle of view of the rigid scope 100 in the upward-downward direction, and MAX_ANGLE_LR is the maximum angle of view of the rigid scope 100 in the rightward-leftward direction. MAX_PIXEL_UD is the maximum number of pixels of the image sensor 240 in the upward-downward direction, and MAX_PIXEL_LR is the maximum number of pixels of the image sensor 240 in the rightward-leftward direction. MV_UD is a motion amount in the surface upward-downward direction. MV_LR is a motion amount in the rightward-leftward direction.

The orthogonal-to-surface component of a change in position (motion in the real space) is used as the orthogonal-to-surface motion amount. Therefore, the orthogonal-to-surface motion amount according to the third embodiment has a sign and a magnitude (e.g., −3 mm or +10 mm).

The focus control section 360 accumulates the parallel-to-surface motion amount and the orthogonal-to-surface motion amount thus acquired to perform control that is similar to that in the second embodiment.

The motion information determination section 390 determines the reliability of motion information based on the motion information output from the motion information acquisition section 380. The motion information reliability thus determined is output to the focus control section 360. For example, the result of the determination is "unreliable" when an absolute value of the motion information exceeds a threshold value. Alternatively, the result of the determination is "unreliable" when the difference between average motion information corresponding to a predetermined number of previous frames and the motion information corresponding to the current frame exceeds a threshold value. The result of the determination is "reliable" when none of these conditions is satisfied.

Although the configuration in which the rigid scope 100 includes the motion sensor 130, and the motion amount acquisition section 380 calculates the motion amount based on the motion signal output from the motion sensor 130, has been described above, the rigid scope 100 may include a position sensor (e.g., magnetic position sensor), and the motion information acquisition section 380 may acquire the motion amount based on a temporal change in position information output from the position sensor.

According to the third embodiment, reflected light from the object is captured as an image using the imaging section 200 that can perform the focus operation, and includes the motion sensor 130 that detects an angular acceleration and an acceleration. The relative motion amount with respect to the imaging section 200 and the object is calculated based on the output from the motion sensor 130. When the net motion amount obtained by accumulating the motion amount over a plurality of frames has exceeded a predetermined threshold value, it is determined that the focus operation is required, and the imaging section 200 performs the focus operation. Since the focus operation is performed when the motion amount obtained by accumulating the motion amount over a plurality of frames has exceeded a predetermined amount, it is possible to implement an AF control process that performs the focus operation when the object has become out of focus even when the motion is slow, and does not perform the focus operation when a momentary motion unintended by the user has occurred.

As described above, the motion information acquisition section 380 acquires the motion information (MV_UD, MV_LR) based on an output value (HEAVE, SWAY, PITCH, YAW) from the motion sensor 130 provided in the imaging section 200. The motion information determination section 390 determines the motion information reliability based on comparison between the motion information and a threshold value for the motion information. For example, the motion information (MV_UD, MV_LR) with an absolute value larger than the threshold value is determined to be "unreliable".

Alternatively, the motion information determination section 390 determines the motion information reliability based correlation between each of a plurality pieces of motion information acquired in time series and motion information before and/or after the motion information. For example, the motion information (MV_UD, MV_LR) is acquired in each frame, and the reliability is determined based on the correlation between the motion information in the j-th frame in the frames, and the motion information in at least one of a (j−1)-th frame or before and a (j+1)-th frame or after. For example, the result of the determination is "unreliable" when the difference between the mean value of the motion information acquired over a predetermined number frames including the j-th frame and the motion information acquired in the j-th frame exceeds a threshold value.

Thus, the output value from the motion sensor 130 is converted into motion information about an object in an image, and whether or not the focus operation is required can be determined based on the motion information. With the reliability determined through comparison using a threshold value, time series correlation, or the like, influence of small movement or the like unintended by the user due to shake or the like can be reduced, and the focus operation can be turned ON for a change of scene requiring the focus operation.

Although the embodiments to which the invention is applied and the modifications thereof have been described in detail above, the invention is not limited to the embodiments and the modifications thereof, and various modifications and variations may be made without departing from the scope of the invention. A plurality of elements described above in connection with the embodiments and the modifications thereof may be appropriately combined to implement various configurations. For example, some of the elements described above in connection with the embodiments and the modifications thereof may be omitted. Some of the elements described above in connection with the embodiments and the modifications thereof may be appropriately combined. Specifically, various modifications and applications are possible without materially departing from the novel teachings and advantages of the invention. Any term cited with a different term having a broader meaning or the same meaning at least once in the specification and the drawings can be replaced by the different term in any place in the specification and the drawings.

What is claimed is:

1. An endoscope apparatus comprising:
a processor comprising hardware, the processor being configured to implement:
  a motion information acquisition process that acquires motion information representing a motion with respect to an imaging section and an object;
  a motion information determination process that determines motion information reliability indicating reliability of the motion information; and
  a focus control process that:
    obtains global motion information about a global relative motion with respect to the imaging section and the object based on the motion information and the motion information reliability;
    determines global motion information reliability indicating reliability of the global motion information based on the motion information reliability;
    obtains cumulative global motion information, as a result of a process of accumulating the global motion information over a plurality of frames; and
    determines whether or not to perform a focus operation to cause the imaging section to bring the object into focus, based on at least one of the cumulative global motion information or the global motion information reliability.

2. An endoscope apparatus comprising:
a processor comprising hardware, the processor being configured to implement:
  a motion information acquisition process that acquires motion information representing a motion with respect to an imaging section and an object;
  a motion information determination process that determines motion information reliability indicating reliability of the motion information; and
  a focus control process that determines whether or not to perform a focus operation to cause the imaging section to bring the object into focus, based on the motion information and the motion information reliability,
  wherein in the motion information acquisition process, the processor is configured to obtain the motion information, which is a plurality of local motion amounts, based on a captured image that is an image of the object captured by the imaging section, and
  wherein in the motion information determination process, the processor is configured to determine the motion information reliability for each of the plurality of local motion amounts.

3. The endoscope apparatus as defined in claim 2, wherein in the motion information determination process, the processor is configured to determine the motion information reliability based on correlation between each of the plurality of local motion amounts and a peripheral local motion amount.

4. The endoscope apparatus as defined in claim 2, wherein in the motion information determination process, the processor is configured to determine the motion information reliability based on brightness of the captured image in an area corresponding to each of the plurality of local motion amounts.

5. The endoscope apparatus as defined in claim 2, wherein each of the local motion amounts is a motion vector, and
wherein in the motion information determination process, the processor is configured to determine the motion information reliability based on correlation between a pixel value of one pixel or more corresponding to an initial point of the motion vector and a pixel value of one pixel or more corresponding to a terminal point of the motion vector.

6. An endoscope apparatus comprising:
a processor comprising hardware, the processor being configured to implement:
  a motion information acquisition process that acquires motion information representing a motion with respect to an imaging section and an object;
  a motion information determination process that determines motion information reliability indicating reliability of the motion information; and
  a focus control process that determines whether or not to perform a focus operation to cause the imaging section to bring the object into focus, based on the motion information and the motion information reliability,
  wherein in the focus control process, the processor is configured to:
    obtain cumulative global motion information, as a result of a process of accumulating global motion information representing a global relative motion with respect to the imaging section and the object over a plurality of frames, based on the motion information and the motion information reliability;
    determine whether the cumulative global motion information is larger than a threshold value for the cumulative global motion information; and
    perform the focus operation to cause the imaging section to bring the object into focus in response to determining that the cumulative global motion information is larger than the threshold value for the cumulative global motion information.

7. The endoscope apparatus as defined in claim 6,
wherein in the focus control process, the processor is configured to:
  determine global motion information reliability, indicating reliability of the global motion information, based on the motion information reliability; and
  not perform the process of accumulating the global motion information for a frame with the global motion information reliability determined to be lower than a threshold value for the global motion information reliability.

8. The endoscope apparatus as defined in claim 6,
wherein in the focus control process, the processor is configured to not perform the process of accumulating the global motion information for a frame in which a motion amount represented by the global motion information is determined to be smaller than a threshold value for the global motion information.

9. The endoscope apparatus as defined in claim 6,
wherein in the focus control process, the processor is configured to:
  determine global motion information reliability, indicating reliability of the global motion information, based on the motion information reliability; and
  perform for a frame with the global motion information reliability determined to be lower than a threshold value for the global motion information reliability, a process of accumulating as the global motion information in the frame, the global motion information in a frame before the frame.

10. The endoscope apparatus as defined in claim 6, wherein in the focus control process, the processor is configured to:
- determine global motion information reliability, indicating reliability of the global motion information, based on the motion information reliability; and
- perform for a frame with the global motion information reliability determined to be lower than a threshold value for the global motion information reliability, a process of accumulating as the global motion information in the frame, predetermined global motion information.

* * * * *